United States Patent [19]
Karlson

[11] Patent Number: 5,868,999
[45] Date of Patent: Feb. 9, 1999

[54] OZONE STERILIZER AND METHOD FOR OZONE STERILIZATION

[75] Inventor: Eskil L. Karlson, Erie, Pa.

[73] Assignee: Ozone Sterilization Products, Inc., New City, N.Y.

[21] Appl. No.: 590,549

[22] Filed: Mar. 19, 1996

[51] Int. Cl.⁶ .............................. A61L 2/20; C01B 13/11
[52] U.S. Cl. .............................. 422/30; 422/33; 422/114; 422/186.11; 422/186.12; 422/292; 261/DIG. 42
[58] Field of Search ................................ 422/28, 186.12, 422/186.19, 186.2, 292, 33, 3, 30, 114; 261/DIG. 42

[56] References Cited

U.S. PATENT DOCUMENTS

| | | | |
|---|---|---|---|
| 1,096,991 | 5/1914 | Blanchard | 422/292 X |
| 1,579,162 | 3/1926 | Strake | 422/186.16 X |
| 2,248,713 | 7/1941 | Locke | 422/121 |
| 2,936,279 | 5/1960 | Rindtorff et al. | 422/186.15 |
| 3,010,892 | 11/1961 | Axt | 422/186.2 |
| 3,023,155 | 2/1962 | Castor | 422/186.18 |
| 3,516,223 | 6/1970 | Andersen et al. | 53/512 |
| 3,549,528 | 12/1970 | Armstrong | 422/28 X |
| 3,704,096 | 11/1972 | Verses et al. | 422/3 X |
| 3,719,017 | 3/1973 | Shapiro | 422/28 X |
| 3,751,225 | 8/1973 | Karlson | 422/116 |
| 3,766,051 | 10/1973 | Bollyky | 422/186.19 |
| 3,899,685 | 8/1975 | Francis et al. | 422/186.16 |
| 4,013,567 | 3/1977 | Emelyanov et al. | 422/186.19 |
| 4,025,441 | 5/1977 | Tabata et al. | 422/186.19 |
| 4,051,043 | 9/1977 | Harter et al. | 422/186.16 |
| 4,051,045 | 9/1977 | Yamamoto et al. | 422/186.16 |
| 4,079,260 | 3/1978 | Dmitriev et al. | 422/186.19 |
| 4,234,800 | 11/1980 | Kenly et al. | 422/186.19 |
| 4,417,966 | 11/1983 | Krauss et al. | 422/186.15 X |
| 4,517,159 | 5/1985 | Karlson | 422/20 |
| 4,666,649 | 5/1987 | Masuda et al. | 422/186.2 |
| 4,869,881 | 9/1989 | Collins | 422/186.18 |
| 4,908,189 | 3/1990 | Staubach | 422/186.19 |
| 4,966,666 | 10/1990 | Waltonen | 422/186.04 X |
| 4,988,484 | 1/1991 | Karlson | 422/186.19 |
| 5,002,738 | 3/1991 | Pin et al. | 422/186.13 |
| 5,008,087 | 4/1991 | Batchelor | 422/186.22 |
| 5,069,880 | 12/1991 | Karlson | 422/186.19 |
| 5,087,419 | 2/1992 | Lutz | 422/28 |
| 5,120,512 | 6/1992 | Masuda | 422/297 |
| 5,160,700 | 11/1992 | Anderson et al. | 422/34 |
| 5,169,606 | 12/1992 | Batchelor | 422/186.19 |
| 5,184,633 | 2/1993 | Langford | 422/292 X |
| 5,207,237 | 5/1993 | Langford | 134/102.1 |
| 5,266,275 | 11/1993 | Faddis | 422/28 X |
| 5,334,355 | 8/1994 | Faddis | 422/122 |
| 5,344,622 | 9/1994 | Faddis et al. | 422/306 |
| 5,464,572 | 11/1995 | Bonzi | 261/DIG. 48 X |

OTHER PUBLICATIONS

E.B. Baumeister et al., "Fluid Particle Heat Transfer in Packed Beds," *A.I.Ch.E. Journal,* vol. 4, No. 1 (Mar. 1958), pp. 69–74.

A.S. Gupta et al., "Direct Analogy Between Mass and Heat Transfer of Beds of Spheres," *A.I.Ch.E. Journal,* vol. 9, No. 6 (Nov. 1963), pp. 751–754.

T.E.W. Schumann, "Heat Transfer: A Liquid Flowing Through a Porous Prism," *J.F.I.* (Sep. 1929), pp. 405–416.

*Primary Examiner*—E. Leigh McKane
*Attorney, Agent, or Firm*—Panitch Schwarze Jacobs & Nadel, P.C.

[57] ABSTRACT

An ozone sterilizer includes a generator capable of generating a gas containing at least about 10% by weight ozone, a holding tank, a humidification chamber for receiving the ozonated gas and humidifying it to form a sterilant including at least about 8% by weight ozone at a humidity of at least about 60%, a vent for bleeding sterilant from the humidification chamber over a first catalyst, a sterilization chamber for receiving a controlled flow of sterilant which is in fluid communication with a pump for evacuating the sterilization chamber over a second catalyst, a vent for bleeding the sterilant from the sterilization chamber and a heater for providing warm air drawn into the sterilization chamber by the pump.

19 Claims, 12 Drawing Sheets

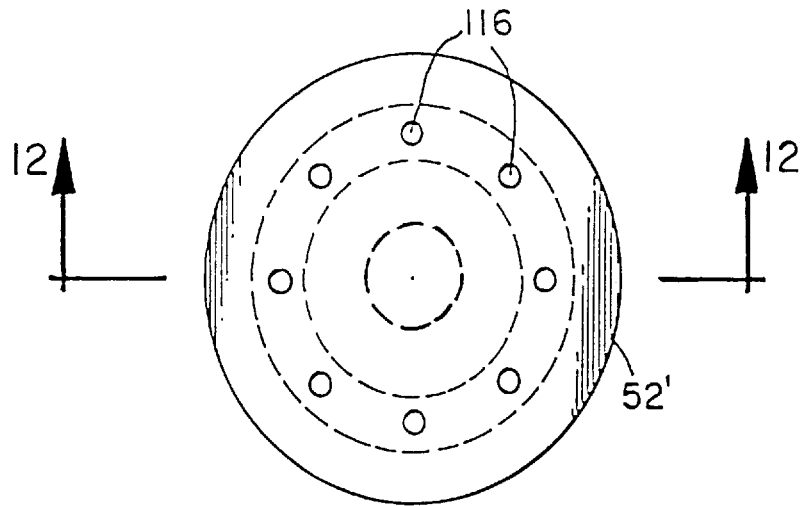
FIG. 11
FIG. 12
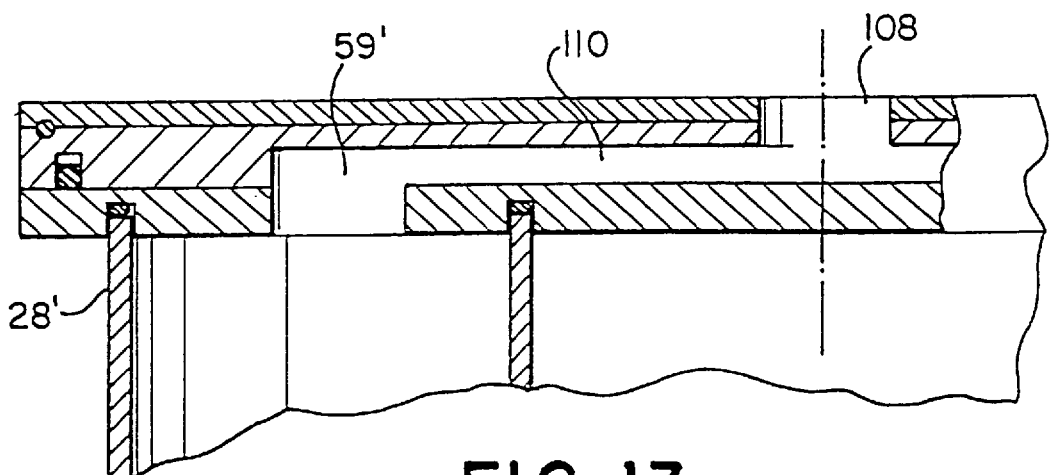
FIG. 13

OZONE STERILIZER AND METHOD FOR OZONE STERILIZATION

FIELD OF THE INVENTION

The present invention relates to the field of ozone generation and sterilization using ozone. More particularly, it relates to a method and apparatus for generating ozone and a method and apparatus for sterilizing articles with an ozone sterilant.

BACKGROUND OF THE INVENTION

Hospitals and related medical institutions, doctors' offices and various chemical and medical laboratories all require sterilization equipment. Because high pressure steam destroys heat and moisture sensitive medical instruments, the vast majority of such institutions sterilize those instruments with a "cold" sterilization system based on ethylene oxide. Although ethylene oxide is an effective sterilant, it has three primary deficiencies.

First, the highly flammable nature of ethylene oxide requires its combination with chlorofluorocarbons (CFCs). Because CFCs have been shown to be destructive of the ozone layer, worldwide environmental regulations, e.g., the Montreal Protocol, prohibit CFC production in all major industrial nations after Dec. 31, 1995. As a result, the generally used mixture of 12% ethylene oxide and 88% CFC is effectively banned from the market place.

Second, ethylene oxide gas is neurotoxic and has been classified by OSHA as a carcinogenic substance. As a result, the use of ethylene oxide in hospitals will soon be eliminated independently of the CFC problem.

Finally, the natural properties of ethylene oxide that make it an effective sterilant also require that there be a prolonged aeration period (typically 12–18 hours) to eliminate the toxic residue of ethylene oxide on sterilized articles. The extended aeration period makes it impossible to effectively sterilize large numbers of medical instruments rapidly. This is becoming a significant problem particularly in hospitals and similar institutions where medical treatment is becoming more directed towards same-day procedures and ambulatory surgery.

While some alternative methods to the use of ethylene oxide have recently been introduced, including plasma-gas systems based on peracetic acid and on hydrogen peroxide, none provides a truly acceptable alternative to ethylene oxide which is effective, safe and inexpensive.

While ozone gas in general and humidified ozone gas in particular, have been in use in purification for many years, two principle problems have been associated with its use as a medical instrument sterilant, namely, the difficulties encountered in (1) generating ozone of a sufficiently high concentration and humidity to kill microorganisms and (2) maintaining a continuous flow of such humid, high-concentration ozone for a sufficiently long period of time to penetrate the protective bacterial membranes.

Ozone is an unstable substance which easily degrades to oxygen in the presence of heat or in water. Ozone may be generated several ways, the most common of which is by passing an oxygen-containing gas through a zone between two electrodes and generating a corona discharge between the electrodes. One of the electrodes is a high voltage metal electrode and the other is generally a conductor coated on a dielectric such as glass or ceramic. The first electrode is typically grounded at a high voltage transformer ground and the second electrode is generally electrically attached to the high voltage terminal of a high voltage transformer.

The corona discharge splits the natural oxygen molecules into individual, highly active oxygen atoms, which immediately combine with the nearest oxygen molecule to form a trioxygen molecule, i.e., ozone. The reaction is extremely fast and exothermic. The heat of the reaction, the heat generated by the corona discharge and the heat generated within the dielectric by the passage of current contribute directly to the destruction of the newly generated ozone.

Sterilization is enhanced by the use of humidified ozone. The ozone penetrates the membrane of the bacteria readily when the bacteria is coated with a water film which results from the required humidity level. The penetration of ozone requires less energy when it first passes through hydroxide and when it passes through the bacterial membrane when using a water film as a transfer medium. The water film transfer medium acts in the manner of an impedance transformer, whereby only a small amount of the ozone's molecular energy is required to pass through the bacterial membrane.

Prior art ozone sterilizers which used humidified ozone as a sterilant do not consistently achieve levels of greater than 6% ozone by weight in the humidified sterilant due to heat build-up in the generator.

To increase the quantity and outlet ozone concentration, various attempts have been made to increase the level of cooling and thereby the amount of ozone conversion in the generator. These attempts include feeding cold oxygen to the generator as in U.S. Pat. No. 5,002,738; feeding cold oxygen to one of two parallel annular ozone generation zones such that all of the ozonated gas from a first annular zone must pass through a second annular generation zone before leaving the generator as in U.S. Pat. Nos. 5,008,087, 5,169,606 and 2,936,279; and passing oxygen through a helically-shaped dielectric as in U.S. Pat. No. 4,966,666.

In constructing ozone sterilizers in the past, unsuccessful efforts have been made to increase the rate of conversion from oxygen into ozone by attempting to devise methods of preventing the exothermic heat from destroying the generated ozone formed in the generator.

A further method of increasing conversion rates is by making the generators significantly larger in size. However, larger generators require large quantities of power which not only increases costs, but more importantly, results in significantly higher quantities of ozone-destroying heat. Further, a larger size generator would not be practical in many institutions requiring sterilizers.

Accordingly, it would be beneficial to develop an ozone sterilizer and generator that achieve a high conversion rate without significant loss of ozone in either the generator or the humidification procedure.

Further, it would be advantageous to increase the time that oxygen-containing gas used to form ozone resides in the portion of an ozone generation zone that has the highest ionization energy, i.e., nearest the electrodes, to increase the production of ozone. By increasing the production rate, and minimizing the loss due to generator heat and humidification, ozone sterilizers may be made more efficient and practical.

In view of the incipient disappearance of ethylene oxide as a sterilant, as described above, as well as the apparent lack of success of current alternative processes, there is a need in the art, particularly, the medical and scientific fields, for an efficient and effective ozone generator and sterilizer using a sustained flow of very humid, high-concentration ozone in a safe and controlled manner. There is a need in the art for an ozone sterilizer that is inexpensive to operate, has a short sterilization cycle with a high bacteria kill rate and can produce a high concentration of ozone that can be effective in a large as well as a small sterilization apparatus. Finally, there is a need for an apparatus and method for generating ozone at sufficiently high quantities for introduction into a humidifier such that a controlled amount of an effective humidified ozone sterilant is provided to achieve a high bacteria kill rate in as short a time as possible.

SUMMARY OF THE INVENTION

The present invention includes an apparatus for generating ozone and a method for generating a gas containing ozone. The apparatus includes an ozone generator, a means for generating a corona discharge, a heat exchanger, a conduit for partially circulating a portion of the gas leaving the generation zone of the generator, and a circulation pump. In the apparatus, a portion of ozone-containing gas leaving the generation zone is circulated through the heat exchanger and combined with an oxygen-containing gas forming a feed gas. The cool feed gas is fed to the generation zone of the generator and used in the zone to form further ozone. The feed gas cools the interior of the generator and increases the concentration of ozone in the gas leaving the generator.

The ozone generator has a first electrode and a second electrode. The electrodes are spaced from each other and define between them the ozone generation zone. The inlet of the zone receives the feed gas comprising oxygen, and the outlet of the zone releases a gas mixture of the feed gas and ozone which is generated in the zone. A first coolant is in heat exchange relation with one surface of the first electrode. The heat exchanger has a gas side and a first coolant side. The gas side is in fluid communication with the zone. A second coolant in the first coolant side acts to cool the gas circulated through the gas side of the heat exchanger. The conduit is in fluid communication between the zone and the gas side of the heat exchanger and is configured for receiving a portion of the gas mixture which leaves the outlet of the zone. The pump circulates the portion of the gas mixture through the conduit, the heat exchanger and the zone.

In the method for generating ozone, a feed gas comprising oxygen, as described above, is introduced into the ozone generation zone in an ozone generator. A corona discharge is created between a first and second electrode in the generator to form ozone within the zone from the oxygen in the feed gas. A surface of the first electrode is cooled with a first coolant. A mixture of ozone and feed gas is released from the zone, and a portion of that mixture is drawn through a heat exchanger to be cooled. The first portion of the mixture drawn through the heat exchanger is combined with a gas comprising oxygen to form the feed gas.

The present invention also includes an ozone sterilizer and a method for sterilizing an article. The ozone sterilizer includes an ozone generator, a holding tank, a humidification chamber, a sterilization chamber, a first and a second vent for the humidification and sterilization chambers, respectively, means for controlling gas flow from the humidification chamber to the sterilization chamber, a heater and pump means. The ozone generator is capable of generating a gas comprising at least about 10% by weight ozone. The holding tank is in fluid communication with the generator and receives the gas comprising ozone from the generator. The holding tank also prevents backflow of moisture into the generator. The holding tank is also in fluid communication with the humidification chamber. The humidification chamber receives the gas comprising ozone from the holding tank and humidifies the gas to form a sterilant. The sterilant contains at least about 8% by weight ozone at a humidity of at least about 60%. The first vent bleeds sterilant from the humidification chamber and the second vent bleeds sterilant from the sterilization chamber. The vents bleed the sterilant over a first catalyst which converts ozone to oxygen. The sterilization chamber is in fluid communication with and receives sterilant from the humidification chamber. The gas flow into the sterilization chamber from the humidification chamber is controlled by the control means. The heat provides warm air to the sterilization chamber. The pump means flows air into the sterilization chamber and evacuates the chamber over a second catalyst which, like the first catalyst, converts ozone to oxygen.

The method for sterilizing articles includes placing the article in the sterilization chamber and sealing the chamber. The chamber is at least partially evacuated and the sterilization cycle begins. A controlled flow of the sterilant gas, as described above, is introduced into the chamber until the chamber is at about ambient pressure. The sterilant circulates in the chamber, and continuously flows into the chamber after ambient pressure is reached, while the sterilant is simultaneously bled from the chamber over the first catalyst for a first predetermined time period. The first catalyst converts ozone to oxygen. The chamber is once again at least partially evacuated and the sterilant reintroduced as described above for a predetermined number of cycles. The chamber is then evacuated over a second catalyst to convert ozone to oxygen and an aeration cycle begins. In the aeration cycle, filtered, heated air is drawn into the chamber until the chamber is at about ambient pressure. Once ambient is reached, the air continuously flows through the chamber, while being simultaneously bled over the second catalyst for a second predetermined period of time. The chamber is then unsealed and the articles removed from the chamber.

BRIEF DESCRIPTION OF THE DRAWINGS

The foregoing summary, as well as the following detailed description of preferred embodiments of the invention, will be better understood when read in conjunction with the appended drawings. In the drawings, like numerals are used to indicate like elements throughout. For the purpose of illustrating the invention, there are shown in the drawings embodiments which are presently preferred. It should be understood, however, that the invention is not limited to the precise arrangements and instrumentalities shown. In the drawings:

FIG. 11 is a top sectional view of a seal used in a generator in the multiple-generator apparatus of FIG. 7 taken along line 11—11;

FIG. 12 is a cross sectional view of the seal of FIG. 11 taken along line 12—12;

FIG. 13 is a partially broken away enlarged cross sectional view of the top portion of an outlet of a multiple-generator apparatus in accordance with the invention;

DETAILED DESCRIPTION OF PREFERRED EMBODIMENTS

Figure 1:
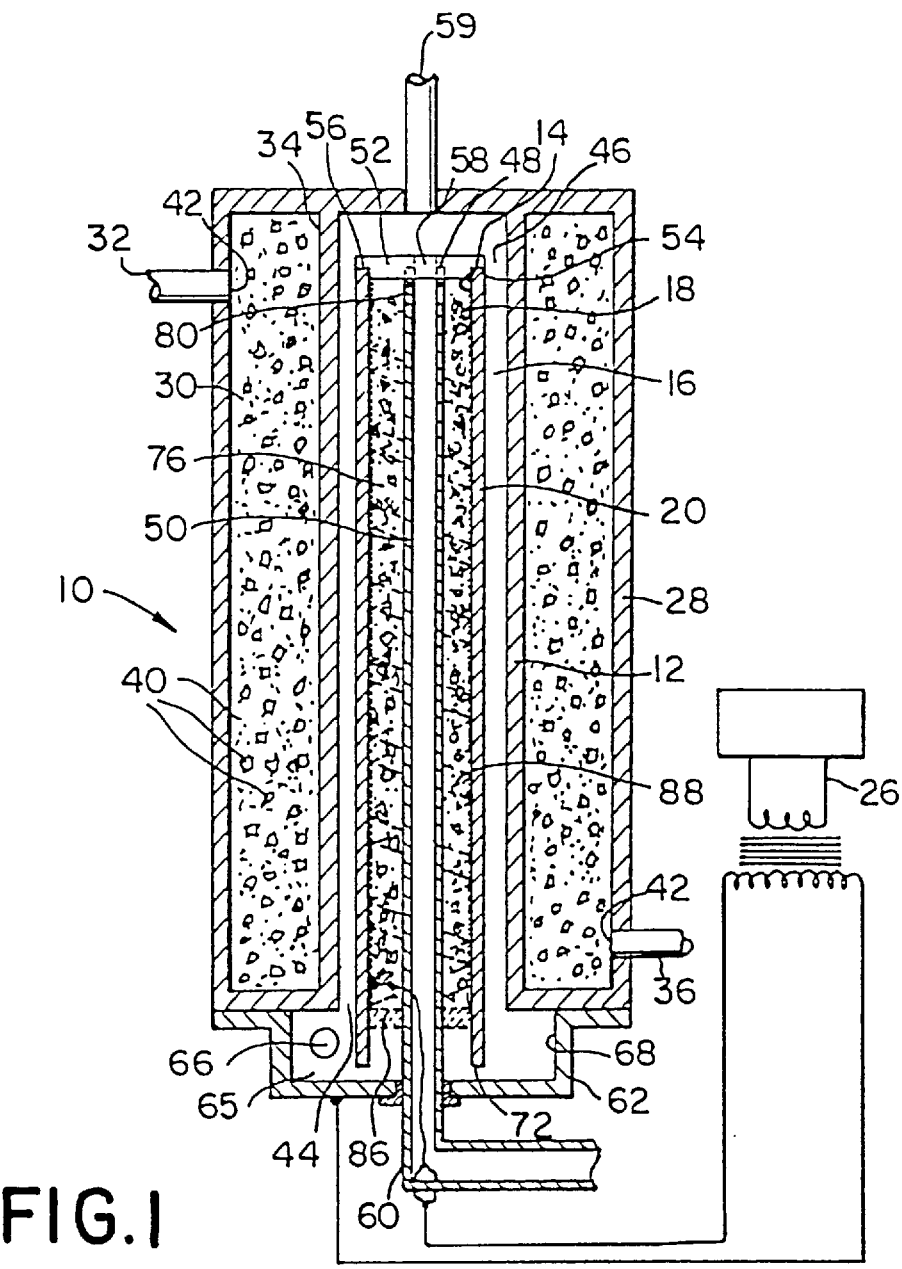
FIG. 1 is a cross-sectional simplified representation of an ozone generator according to the invention.

Certain terminology is used in the following description for convenience only and is not limiting. The words "right," "left," "lower," "upper," "inner" and "outer" designate directions in the drawings to which reference is made. The terminology includes the words above specifically mentioned, derivatives thereof, and words of similar import.

The invention provides a highly efficient, economical ozone generator which provides a continuous flow of ozonated gas having a high percentage concentration of ozone. The generator is highly efficient as a result of the continuous partial recirculation of ozonated gas formed in the generator, the highly efficient cooling system and the swirling flow of feed gas within the ozone generator. As a result of the high efficiency of the generator, it is capable of being used in a small sterilizing apparatus of only 2 ft$^3$ as well as larger units of up to about 12 ft$^3$. The sterilizer includes a humidifier which provides a humidified-ozone gas sterilant having a high percentage concentration of ozone such that fewer sterilization cycles are necessary, sterilization cycle time is shorter and bacteria kill rates are higher than prior art ozone sterilizers.

Referring now to the drawings in detail, there is shown in FIG. 1, a simplified cross-sectional representation of an embodiment of an ozone generator for use in an apparatus for generating ozone in accordance with the invention. The generator, corona discharge generating means and conduit for gas circulation will be described followed by the remaining features of the apparatus including the heat exchanger and pump means.

The ozone generator, generally referred to as 10, includes a first, annular electrode 12 and a second, central electrode 14 spaced from the first electrode 12 defining an ozone generation zone 16 in the annular space between the electrodes 12, 14. As shown in FIG. 1, the first electrode 12 is a high voltage electrode and is in the form of an outer metal tube. The second electrode 14 as shown in FIG. 1 is a conductive coating 14 on the inside surface 18 of an inner tube 20. The first electrode and the inner tube 12, 20 are arranged concentrically with respect to each other.

While the electrodes 12, 14 as shown are in the form of concentric tubes, the electrodes may also be in the form of parallel plates seated in a pressure vessel and having a cooling fluid in connection with a first electrode and a space between the electrodes. The concentric arrangement is preferred for maximizing the cooling efficiency of the apparatus and for providing a larger annular ozone generation zone 16.

The inner tube 20 is formed of a dielectric insulating material. The dielectric material may be any suitable dielectric material such as, for example, any suitable glass or ceramic dielectric material having a dielectric constant of at least about 10. Preferably, the dielectric insulating material is glass, and more preferably a lead glass. By using a lead glass, the dielectric constant is increased approximately 15% over most standard glass compositions. Increasing the dielectric constant decreases the amount of energy absorbed by the glass such that the glass is not so highly heated. Further, the ozone conversion is enhanced by using a material having a higher dielectric constant such as lead glass, as that material will also decrease the voltage resistance over the inner tube 20 such that more electrical energy is retained in the gas passing through the zone 16 which is subject to cooling as described below.

The second electrode 14 as shown in FIG. 1 is in the form of a conductive coating including a conductive material, for example, a thin layer of anodized silver. The second electrode may be grounded by any suitable means. The electrodes are both connected to the terminals of a means for generating a corona discharge. Any suitable power source may be used for powering the generator which includes means for providing pulses of voltage to the electrodes. As shown in FIG. 1, a transformer 26 is provided for powering the generator. While it is preferred that the electrodes be arranged as shown, it will be understood, based on this disclosure, that either electrode may be the ground electrode by reversing the polarity with respect to the transformer 26.

The transformer 26 is preferably a step-up transformer having a DC power supply connected to a chopper for pulsing the voltage charges from about 2,000 to 40,000 volts. The chopper may have either a constant frequency of from about 300 to about 8,000 Hz, preferably about 350 Hz, or a variable frequency range of from about 300 to about 1,000 Hz, preferably between about 300 and 500 Hz. If a constant chopping frequency is provided, the voltage input may be controllable by an AC current from a central processing unit which is input to a DC rectifier for providing the DC supply to the chopper.

A central processing unit can be programmed to control the ozone concentration in the gas leaving the generator between predetermined minimum and maximum values by turning the DC supply to the chopper on and off in response to the exit ozone concentration as measured by an ozone monitor having an output in connection with an input of the central processing unit. If a variable chopping frequency is used, the chopping frequency may be proportionally varied between minimum and maximum values by an oscillator controlled by a voltage of from about 1–10 volts from the central processing unit with respect to the minimum and maximum ozone concentration levels. The frequency level proportionally increases, if the measured ozone concentration decreases. The higher the frequency, the higher the ozone produced in the generator 10.

Figure 6:
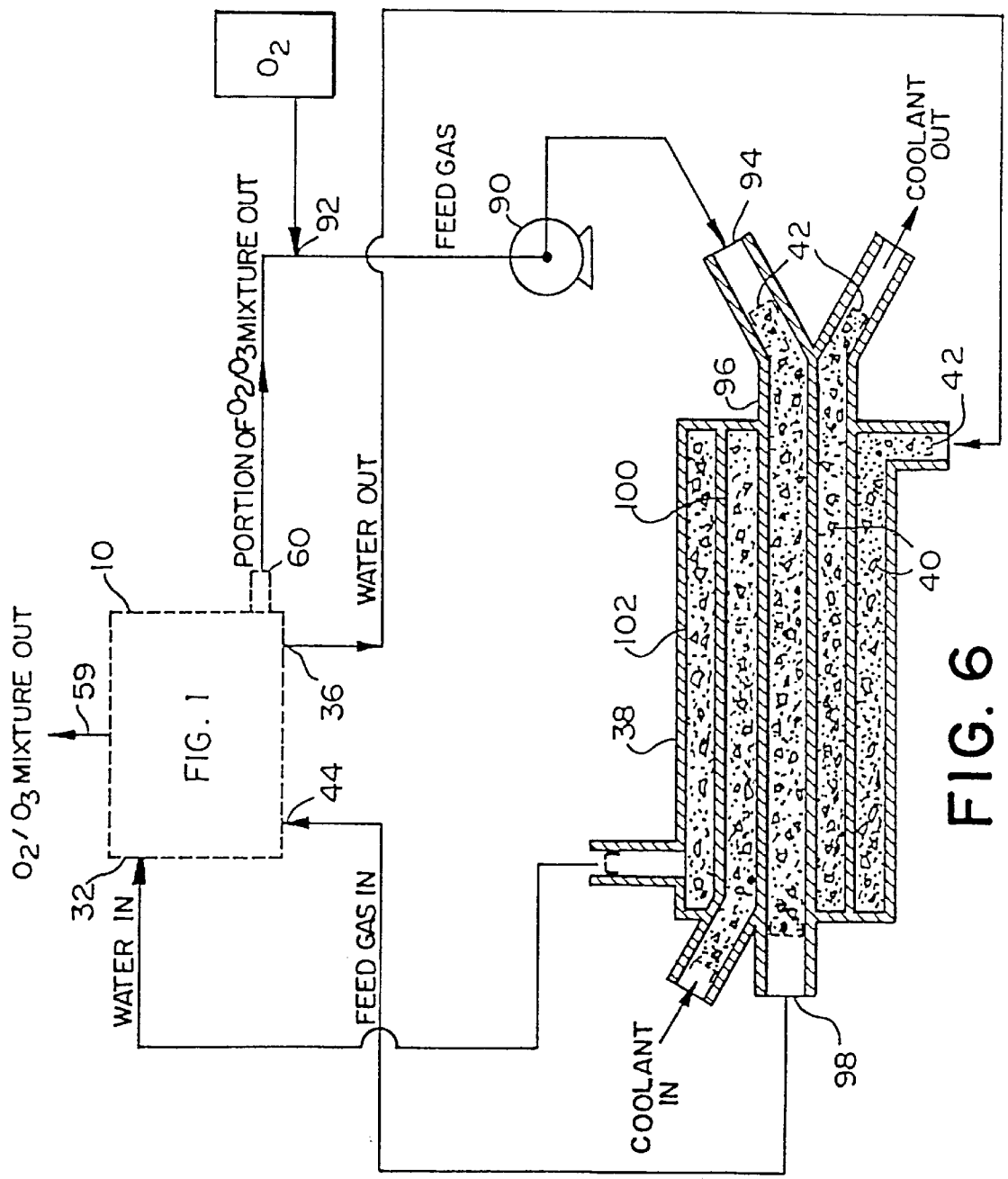
FIG. 6 is a schematic representation of an embodiment of the apparatus for generating ozone of the invention including the ozone generator of FIG. 1 in the broken line.

The generator 10 includes an outer pressure vessel housing 28. The housing 28 as shown in FIG. 1 is cylindrical, however, other housing configurations such as rectangular, spherical and the like may be used. The cylindrical shape is preferred for better gas flow characteristics. The housing 28 preferably surrounds an annular cooling jacket 30 formed between the first electrode 12 and the housing 28 as shown in FIG. 1. The cooling jacket 30 has an inlet 32 for receiving a first coolant in heat exchange relation with the first electrode 12 for cooling the outside surface 34 of the first electrode 12 and an outlet 36 for releasing the coolant. Preferably, the first coolant is water, however, other coolants including ethylene or propylene glycol, brine, silicon oil, chilled gas, including chilled feed gas as described below, or other suitable coolants may be used. It is also conceivable that dry ice or a similar cold solid could serve as the first coolant, however, it is not preferred. While the coolant leaving the outlet may be dumped into a drain, the coolant is preferably recirculated through a heat exchanger and cooled in the heat exchanger 38 for reuse, as shown in FIG. 6.

In an alternative embodiment of the generator, using a modification of the apparatus of FIG. 1, housing 28, would function as the first electrode which, in conjunction with electrode 14, would be used for generating the corona discharge. In such an arrangement, metal tube 12 would be an optional feature and the cooling jacket 30 would include the generation zone 16. Chilled feed gas fed through inlet 32 would serve as the gas to be ozonated as well as the first coolant for cooling the first electrode. The gas would leave outlet 36 and could be recycled through a heat exchanger as described below.

Such feed gas acting as the first coolant, with metal tube 12 present, could also be ozonated in the cooling jacket 30 such that the cooling jacket 30 and zone 16 would both be ozone generating zones. In such an embodiment, the feed gas would be split and fed to both inlet 32 and inlet 44 through opening 66 as discussed below.

In many cases, water or other coolant may be sufficient for cooling the first electrode 12. However, the cooling jacket as shown in FIG. 1, preferably includes a plurality of heat absorbing bodies 40 which may be formed of metals such as, for example, copper, aluminum, zirconium, stainless steel or other similar metals having high heat conductivity and non-corrosive properties, or may be a plated metallic body, such as electroplated copper. The bodies may be chips or smaller fibers of metal but preferably include a mixture of both chips and fibers. The chips, preferably have at least one flat surface, and may range in size from about 1/16 inch to about 1/4 inch in diameter as measured in the longest dimension. The fibers or strands are generally about 1/8 inch long and about 1/32 inch in diameter.

The metallic bodies 40 create better flow distribution of the coolant inside the cooling jacket 30 such that contact between the coolant and the first electrode 12 is increased. The metallic bodies also collectively function as a heat sink, evenly distributing and absorbing heat transferred from the first electrode 12 to the coolant. The metallic bodies are preferably held within the cooling jacket 30 by mesh 42 such as a screen or other porous surface which covers the inlet 32 and outlet 36. The quantity of heat absorbing bodies within the jacket may be varied. However, it is preferred that the jacket 30 be sufficiently packed with bodies to absorb heat and evenly distribute the first coolant, but not to create a pressure drop over the cooling jacket greater than about 2 psi.

The ozone generation zone 16 has an inlet 44 for receiving a feed gas comprising oxygen and an outlet 46 for releasing from the generator a gas mixture of the feed gas and ozone formed in the zone 16. The outlet 46 is in fluid communication with the first end 48 of a conduit 50 situated concentrically within the inner tube 20. The conduit 50 is held concentrically within the inner tube 20 by a seal 52. The seal 52 is configured for holding the first ends 54, 48 of the inner tube and the conduit such that they are seated in sealing relation within concentric recesses 56 within the seal. The seal may be formed of any ozone resistant substance such as neoprene, silicone, fluoroelastomeric rubber and the like. Ozone resistant O-rings are located between the seal and the ends 48, 54 to prevent leaks and to yield in response to thermal expansion of the inner tube 20 and conduit 50. The seal 52 includes an opening 58 aligned with the first end 48 and in fluid communication with the outlet 46.

The first end 48 and conduit 50 are configured to receive a portion of the gas mixture from about 0% to about 30% by volume, and preferably about 5% to about 15% by volume, of the mixture leaving the outlet 46 for recirculation through a heat exchanger 38 (FIG. 6). The remainder of the mixture leaves by way of an outlet 59 of the generator for use in an ozone application such as the sterilizer described in detail below. The first end 48 may have a diameter sized to receive a portion of the gas mixture or preferably has a variable orifice (not shown) inserted within the end for adjustably receiving a portion of the mixture.

Figure 2:
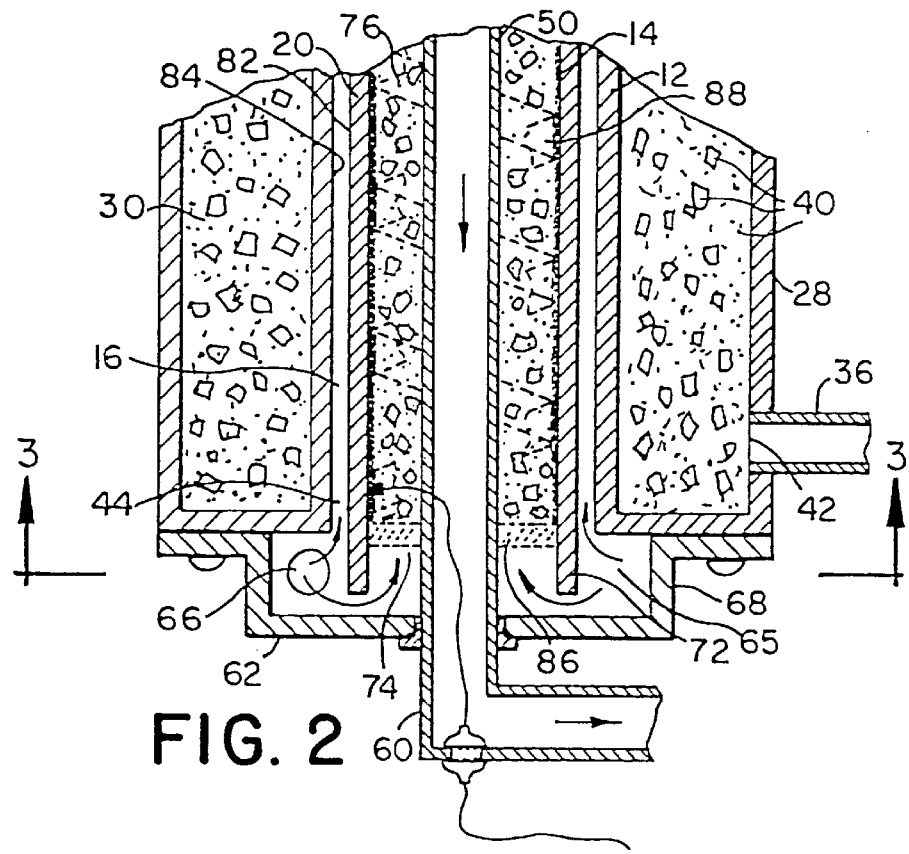
FIG. 2 is an enlarged view of a bottom portion of the generator shown in FIG. 1.
Figure 3:
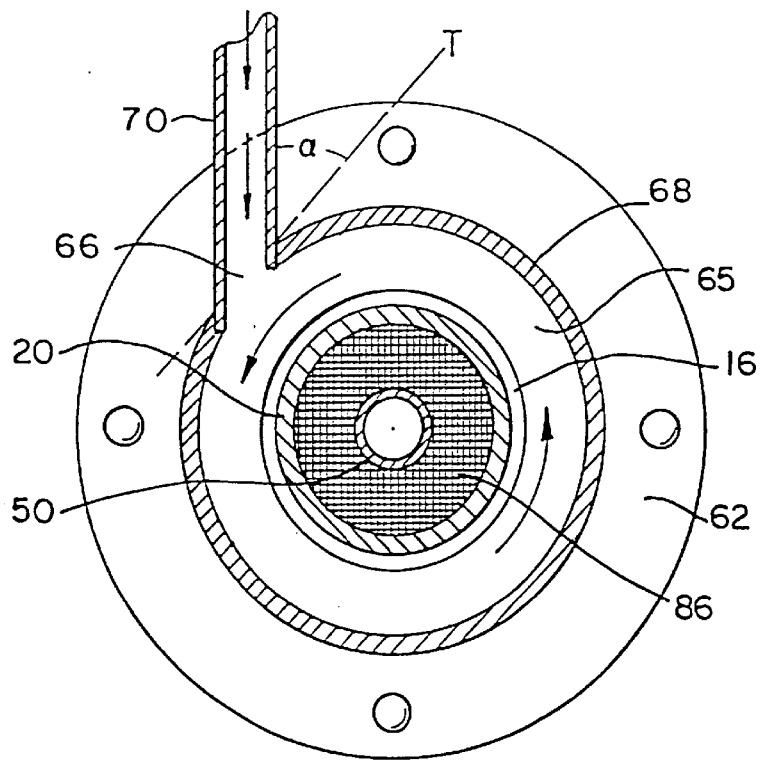
FIG. 3 is a bottom sectional view of the portion of the generator as shown in FIG. 2 taken along line 3—3.

The second end 60 of the conduit 50 extends longitudinally and outwardly through a cylindrical bottom portion 62 of the generator. As best shown in FIG. 2, the inlet 44 is in fluid communication with an annular space 65 in the bottom portion 62 of the generator. The annular space 65 surrounds the conduit 50 in the bottom portion 62 of the generator as best shown in FIGS. 2 and 3. The annular space 65 has an opening 66 extending through a side wall 68 of the bottom portion 62 of the generator. A pipe 70 as shown in FIG. 3 is attached over the opening 66 and forms an acute angle $\alpha$ with a tangent T to the side wall drawn across the opening 66. The angle $\alpha$ is from about 20° to about 45°, preferably, about 30°. Feed gas enters the generator 10 through the pipe 70. The angle provides a generally circular swirling flow through the annular space 65.

The swirling flow through the annular space 65 provides a helical flow upward through the zone 16 at a velocity higher than the velocity which can be achieved with a direct flow of gas through the zone 16. The swirling flow of gas also enters the inner tube 20. This flow pattern provides increased contact of the feed gas with the dielectric tube 20 and first electrode in comparison with straight, direct flow through the zone 16 during one pass through the zone 16. The swirling flow also increases contact of the feed gas with the second electrode 14 when flowing through the tube 20. The results of the swirling effect are cooling of the surfaces of the first electrode and tube 20 as the feed gas flows through the zone 16 and a further cooling of the second electrode 14 as the feed gas flows through the tube 20. In addition, as a result of the cooling effect of the swirled gas flow, a higher yield of ozone per pass through the zone 16 is achieved.

Because ozone is typically best generated where the ionization energy is the most intense, i.e., very near to the facing surfaces of the first electrode 12 and dielectric tube 20, as opposed to the very center of the zone 16, increased flow of available dioxygen molecules very close to or in contact with the facing surfaces of the first electrode 12 and tube 20 increases the ozone production by increasing residence time of the feed gas in this higher ionization region. The annular space 65 should be configured, and the flow rate of the feed gas adjusted such that the volume of gas continuously swirling within the annular space 65 is approximately three times the amount of gas which actually passes upward through the ozone generation zone 16.

The second end 72 of the inner tube 20 extends partially downward into the annular space 65 such that the feed gas flow in the annular space 65 splits and a portion of the feed gas passes through the inlet 74 of an annular chamber 76 defined by the conduit 50, the inner tube 20 and the seal 52. The feed gas, which is cooled prior to entry, flows into the annular chamber 76 and the ozone generation zone 16. The portion of feed gas entering the annular chamber 76 is preferably about 50% to about 99% by volume of the feed gas, more preferably about 70% to about 90% by volume. The portion of the feed gas entering the annular chamber is chilled from the heat exchanger and swirls upward through the chamber 76, cooling the inside surface of the second electrode 14, and exits the annular chamber 76 through at least one aperture 80 in a zone of the conduit proximate the first end 48. The portion of the feed gas is combined with the mixture passing through the conduit and exits the generator through the second end 60 of the conduit for recirculation. The feed gas flowing through the zone 16 cools the facing surfaces 82, 84 of the dielectric 20 and the first electrode 12 respectively.

As shown in FIGS. 1 and 2, a porous surface 86 such as a mesh or screen material is positioned to extend transversely across the inlet 74. The porous surface acts to hold heat absorbing bodies such as the chips and fibers described above within the annular chamber 76. The annular chamber 76 is preferably further packed with a metallic wool, such as copper or aluminum wool, which acts as a further heat sink and which breaks up the flow of the portion of the feed gas through the annular chamber 76 to increase contact of the cooling feed gas with the electrode 14. The cooling efficiency of the cold feed gas passing through the annular chamber 76 is greatly increased by the presence of the metallic wool and/or metallic bodies. While a slight pressure drop of from about 1.3 to about 2 psi occurs over the glass tube 20, the pressure drop is easily compensated for by slightly increasing the pressure of the feed gas by any conventional method, preferably by increasing the pressure of the oxygen-containing gas introduced into the recirculated feed gas mixture. A conductive strip 88, in full contact with the second electrode 14, is coiled around but spaced from the conduit 50 and helps carry the high pulse of current to the second electrode and to act as a further heat sink for the dielectric.

It will be understood by one skilled in the art, based on this disclosure, that the bottom 72 of glass tube 20 could alternatively extend to the bottom 62 of the generator with holes 80 being closed. In such an embodiment, a coolant such as a refrigerant, chilled water and the like could be circulated through annular chamber 76, with or without metallic bodies 40. In such an arrangement all of the swirling inlet flow of feed gas would pass through zone 16 and the gas mixture leaving outlet 46 would still be drawn through conduit 50. The coolant in such a case could be the same as the first coolant used in cooling jacket 30.

As shown in FIG. 6, the apparatus includes a heat exchanger 38 and a pump 90. The pump is positioned for drawing the portion of the gas mixture through the end 60. An inlet 92 for a gas comprising oxygen to be fed into the apparatus is situated between the second end 60 and the pump 90. When the gas comprising oxygen is fed into the gas leaving the end 60, feed gas for the inlet 44 is formed. The gas comprising oxygen may be pure oxygen or oxygen extracted or concentrated from air by any suitable means. Preferably pure oxygen is used from a pressurized source such as an oxygen cylinder.

The pump may be any suitable pump, preferably including an ozone-resistant material, which is capable of forcing the gas through the inlet 94 of a gas side 96 of the heat exchanger 38. The feed gas at a temperature of from about 75° F. to about 100° F. passes through an interior space in the heat exchanger and out through an outlet 98 of the gas side 96 at a temperature of from about 30° F. to about 50° F. The gas side 96 is in fluid communication with the inlet 44. The gas side 96 is in heat exchange relation with a first coolant side 100. A second coolant, preferably a refrigerant at a temperature of from about 25° F. to about 45° F., flows through an interior space of the first coolant side 100. The first coolant side 100 is also in heat exchange relation with a second coolant side 102. The second coolant side 102 cools the first coolant circulating through the cooling jacket 30 which enters the second coolant side 102 at a temperature of about 65° F. to about 90° F. and exits at a temperature of from about 35° F. to about 45° F. The second coolant side 102 is in fluid communication with the inlet 32 and outlet 36 of the cooling jacket 30. The second coolant flows counter-currently to the direction of flow of the feed gas and the first coolant which both flow in parallel through the heat exchanger 38 as best shown in FIG. 6 and in FIG. 15 which schematically shows the flow of gas and coolants through the generator apparatus. The first coolant side 100, the second coolant side 102 and the gas side 96 each preferably include a plurality of heat absorbing bodies 40 as described above in heat exchange relation with the second coolant, the first coolant and the feed gas respectively which may function collectively as a heat sink. The metallic bodies may be held within the sides of the heat exchanger by covering the gas inlet and outlet 94, 98 and the inlets and outlets of the first and second coolant sides with a porous covering or mesh 42 such as that described above with respect to the cooling jacket 30 and annular chamber 76.

Due to the use of the metallic bodies, the heat exchanger has a higher efficiency and requires less heat exchange surface area and/or a lower quantity of coolant flowing through the first and second cooling sides of the heat exchanger. As a result, it can be made smaller. While the metallic bodies are optional in the invention, they are preferred due to the high heat exchange efficiency provided. If the metallic bodies are used in either or both of the cooling jacket 30 or the heat exchanger 38, the water pressure may have to be increased somewhat to compensate for a slight pressure drop of about 1.5 psi over the heat exchanger and from about 0.5 psi to about 2 psi over the cooling jacket. Such a pressure increase can be easily effected by any conventional method such as, for example, adjusting the incoming water pressure, or providing a decreased entry orifice or high pressure nozzle for the water entering the heat exchanger.

Figure 7:
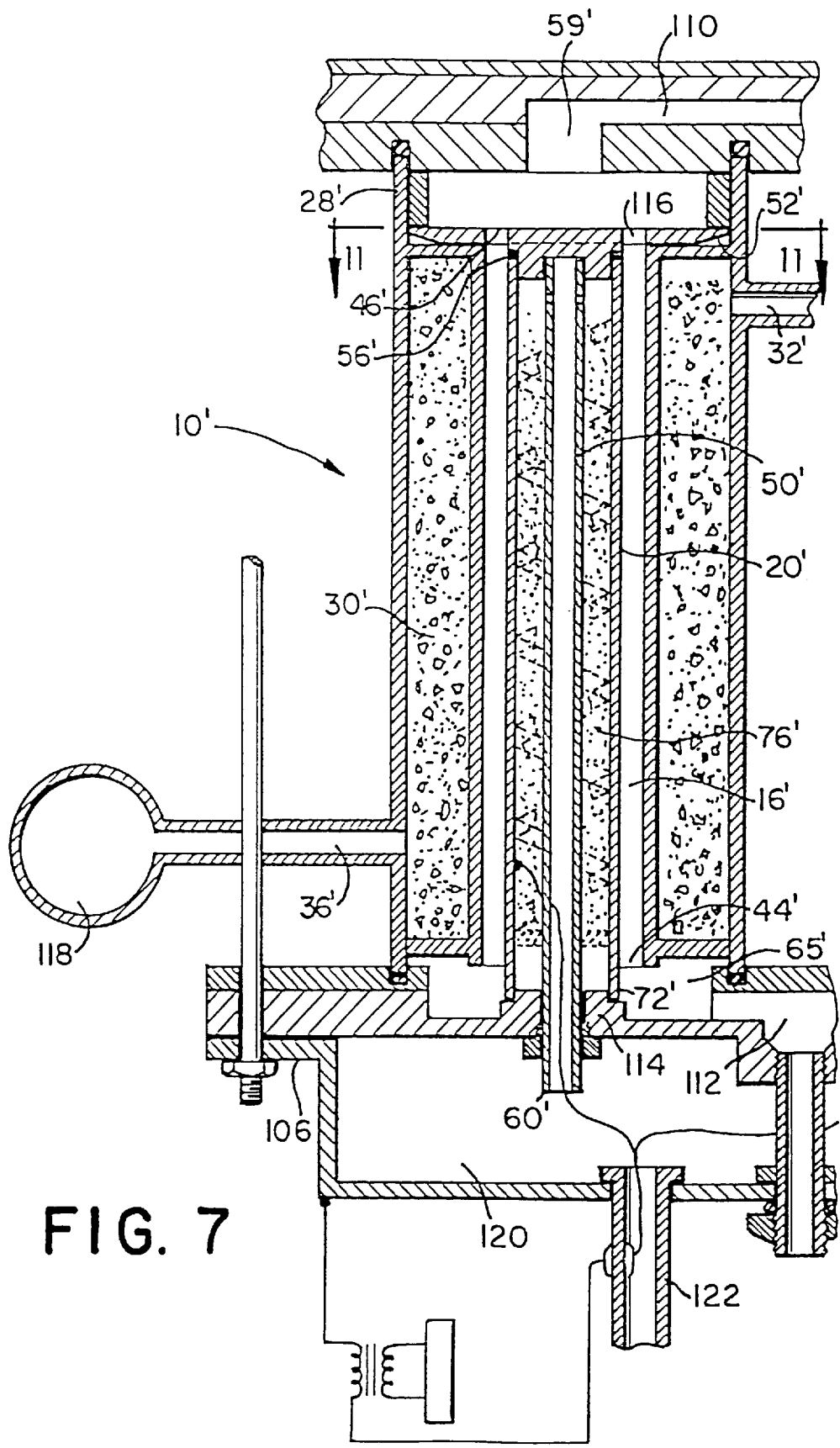
FIG. 7 is a cross-sectional view of one generator in a multiple-generator apparatus according to an embodiment of the invention.
Figure 8:
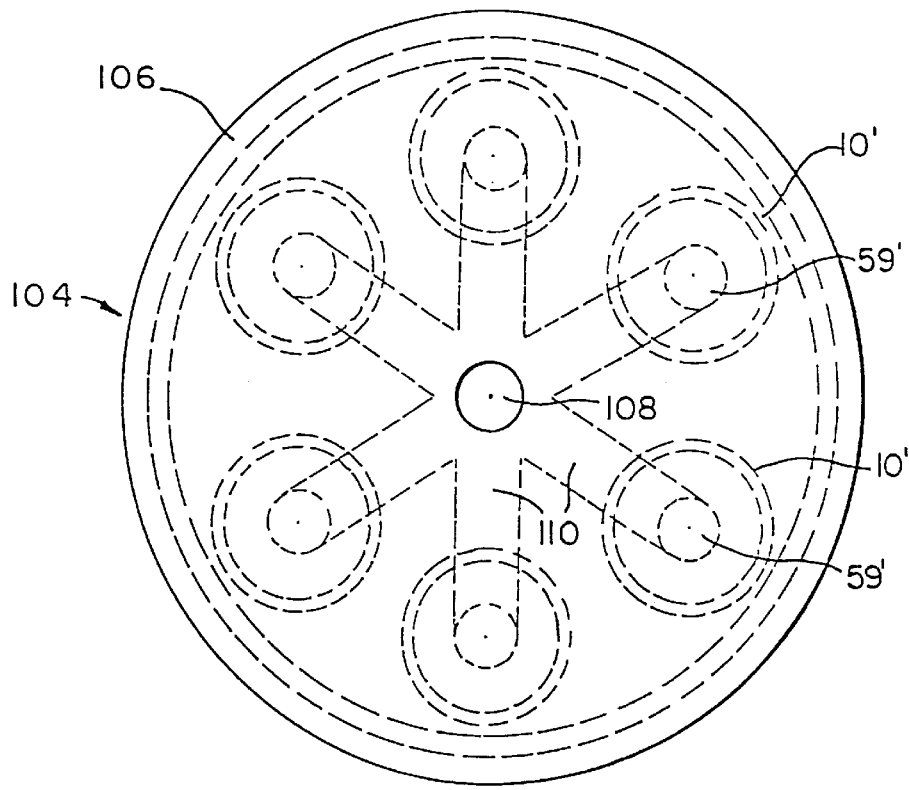
FIG. 8 is a top view of a multiple-generator apparatus according to the invention.

As shown in FIGS. 7–13, the invention further includes a multiple generator apparatus 104. As best shown in FIG. 8, the apparatus 104 includes an exterior vessel 106 having a first outlet 108 for releasing the gas mixture from the vessel 106. The outlets 59' of the individual generators 10' within the apparatus 104 are in fluid communication with the outlet 108 through passageways 110 as shown in FIGS. 8 and 13. In the embodiment as shown, there are six generators 10', however, one skilled in the art will recognize from this disclosure that there may be more or less than six generators depending upon space constraints and the quantity of ozone required for a particular use.

Figure 9:
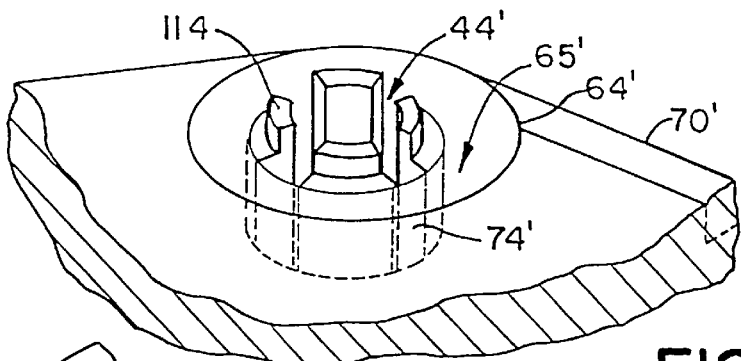
FIG. 9 is a partially broken away perspective view of a feed gas inlet portion of one generator in a multiple-generator apparatus according to the invention.
Figure 10:
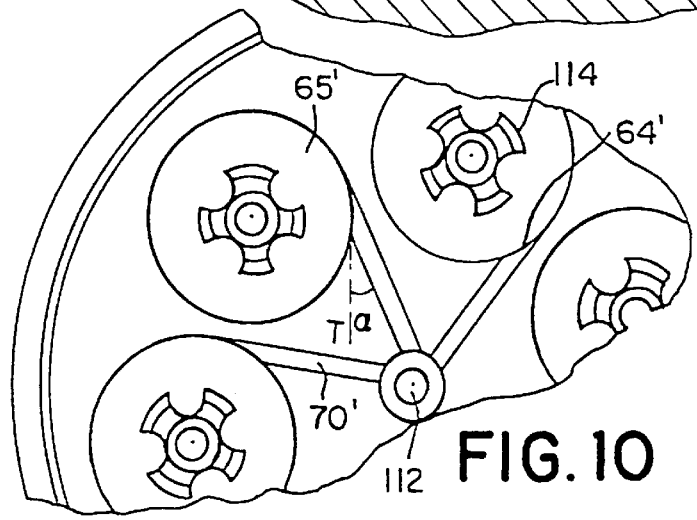
FIG. 10 is a partially broken away bottom view of the feed gas inlets of a multiple-generator apparatus according to the invention.

As best shown in FIGS. 7, 9 and 10, the inlets 44' to the ozone generation zones 16' are in fluid communication with annular spaces 65'. Each annular space 65' includes an opening 64' in fluid communication with a pipe 70' for introducing feed gas. The pipes 70' are connected to a common inlet 112 in fluid communication with the outlet of the heat exchanger 38 for introducing feed gas as shown in FIGS. 7 and 10. The pipes 70' are connected to each opening 64' at an angle α as described above such that the swirling flow of feed gas in each generator can be achieved. As shown in FIGS. 7 and 9, the diverted portion of the feed gas for cooling the inside of the dielectric tube enters the annular chamber 76' of each generator 10' through inlets 74' in the form of gaps created in a bottom seat 114 configured to fit in a sealing manner with the second end 72' of the inner tube 20'.

Seals 52' each extend transversely across the full width of each generator 10'. The seals 52' are shaped to fit within a welded section of an extended outer wall 28' of the generator which is seated within the top portion of the multiple-generator apparatus as shown in FIG. 7. The extended generator wall and the recesses 56' in the seals 52' preferably include O-rings as described above to prevent leaks. The seals 52' have a plurality of openings 116 for allowing the gas mixture to leave the outlet 46' of the ozone generation zone.

The inlet 32' and outlet 36' of the cooling jackets 30' are fed into two main conduits 118 running along the inside and through the bottom of the vessel 106, and running along the outside of the vessel 106, respectively. The conduits are in fluid communication with the heat exchanger 38.

Each of the second ends 60' of the conduits 50' for gas recirculation extends through the bottom of the generator 10' and enters a lower chamber 120 of the vessel 106. Gas leaving the conduits 50' combines in the chamber 120 and exits the vessel 106 through a second central outlet 122 in fluid communication with the inlet of the gas side of the heat exchanger.

Figure 15:
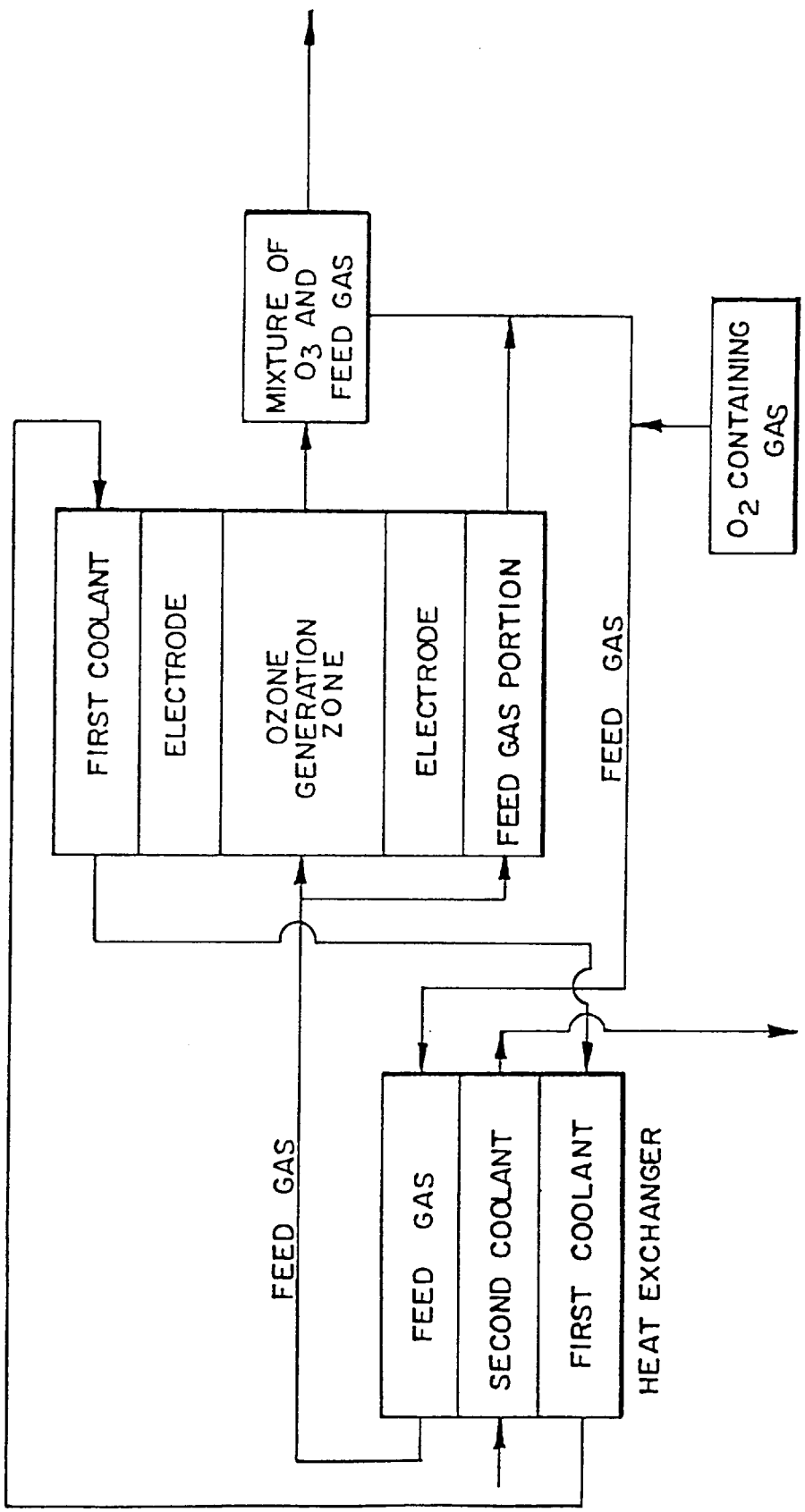
FIG. 15 is a flow diagram of a method for generating ozone in accordance with an embodiment of the invention.

The invention also includes a method for generating ozone as best shown in FIGS. 1, 6 and 15. In the method, a feed gas comprising oxygen is introduced into an ozone generation zone 16 between the facing surfaces 82, 84 of the first and second electrodes 12, 14. A corona discharge is created between the electrodes 12, 14 forming ozone within the ozone generation zone. The surface 34 of the first electrode 12 opposite the zone 16 is cooled with a first coolant. A mixture of the ozone generated in the ozone generation zone and the feed gas is released from the zone 16. A portion of the feed gas is preferably directed away from zone 16 and used for cooling an inside surface 18 opposite the zone 16 of the second electrode 14. The portion directed away is described above.

A first portion of the mixture is drawn through a conduit 50 as described above and a second portion is released from the generator 10 through outlet 59. The first portion of the mixture drawn through the conduit 50 is combined with a gas comprising oxygen forming the feed gas for the generator 10. Preferably, the first portion of the mixture is also combined with the portion of the feed gas directed away from zone 16 for cooling the second electrode 14 and tube 20.

The feed gas is forced through a gas side 96 of a heat exchanger 38 in heat exchange relation with a first coolant side 100 thereby cooling the feed gas prior to introducing it into the inlet 44 for cooling the facing surfaces 82, 84 of the electrodes 12, 14. The first coolant is preferably passed in parallel flow through a second coolant side 102 of the heat exchanger 38. The second coolant side being as described above. A second coolant is passed countercurrently to the flow of feed gas through the gas side of the heat exchanger. In addition, the first coolant, the feed gas and the second coolant are preferably flowed through a plurality of metallic bodies, as described above, situated in each side of the heat exchanger.

The recirculation through the heat exchanger and generation of ozone as described above are repeated continuously until ozonated gas is no longer needed. The quantity of ozone required in the exit gas mixture will be a function of the particular application for which the ozone gas is used. In the case of an ozone sterilization application, it will depend upon the quantity of articles to be sterilized in a particular sterilization load and the degree of contamination of the articles. The ozone generator of the invention is capable of generating ozone at concentrations of from about 9% to about 15% by weight, and at least about 10% by weight, at pressures of from ambient to about 250 psia, preferably from ambient to about 100 psia. More preferably, the ozone generating apparatus generates ozone at a concentration of at least about 14% at a relative humidity of at least about 60%.

The multiple generator apparatus 104 and methods for generating ozone as described above may similarly be altered with respect or the arrangement of electrodes 12, 14, the choice of coolants and the circulation of cooled feed gas or a similar coolant through annular chamber 72 as described above with respect to generator 10.

Alternative embodiments of the sterilizer apparatus, generally referred to as 11, are shown schematically in FIGS. 4, 4a, 4b and 5. The sterilizer includes an ozone generator. The generator may be any generator capable of generating an ozonated gas including at least about 10% ozone. Preferably, the generator is the same as the generator 10 or the multiple-generator apparatus 104 as described above. For the purposes of describing the alternative embodiments of the sterilizer, the generator for the sterilizer apparatus will be referred to as the generator 10; however, it will be understood from this disclosure that the generator 104, or other generators capable of generating an ozonated gas including at least about 10% by weight ozone, may be substituted for the generator 10, and are within the scope of this invention.

The generator 10 receives feed gas from the gas side outlet of a heat exchanger. The heat exchanger is preferably the same as the heat exchanger 38 as described above; however, other heat exchanger configurations may be substituted without departing from the spirit of this invention.

Figure 4:
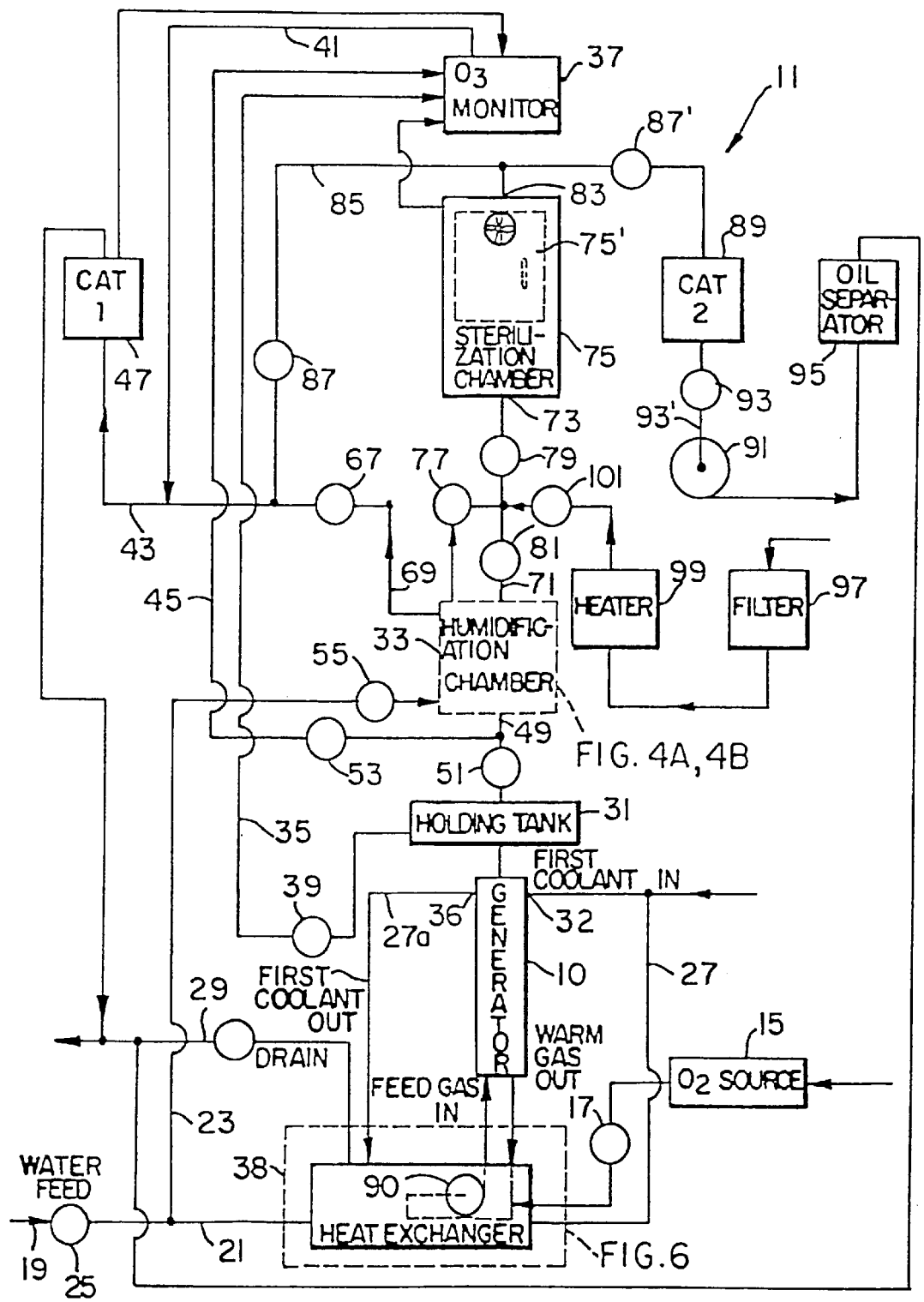
FIG. 4 is a flow diagram of an ozone sterilizer according to one embodiment of the invention.
Figure 14:
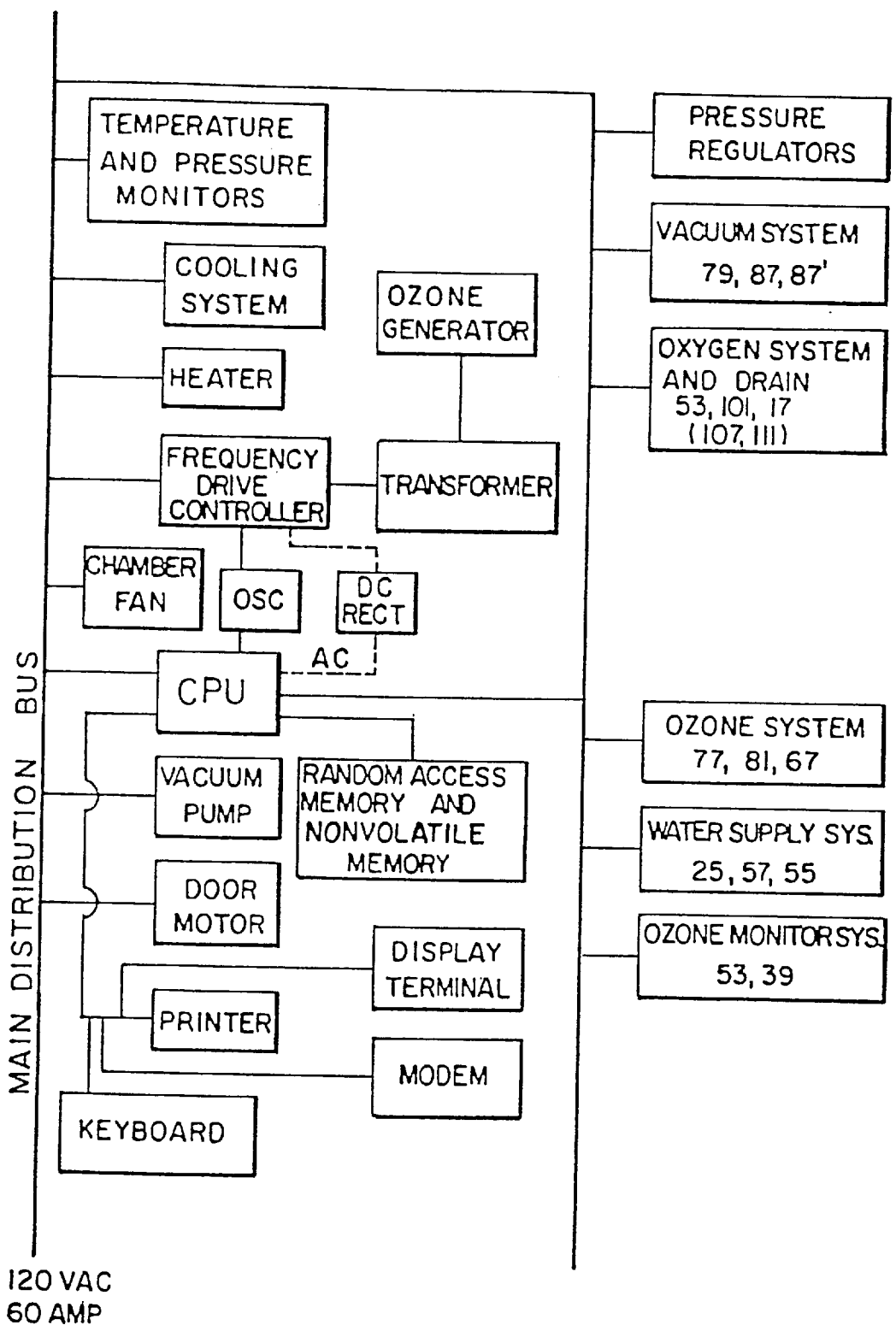
FIG. 14 is a flow diagram of the electrical and control system including the central processing unit of the invention.

As shown in FIG. 4, the warm gas leaving the generator 10 is preferably combined with a fresh feed of oxygen-containing gas from a gas source 15 at the inlet to the heat exchanger unit 38 prior to a pump 90 or a similar forcing means. The oxygen-containing gas is fed into the heat exchanger 38 through a regulating valve assembly 17 which preferably includes a standard pressure regulator, a solenoid valve, a pressure switch, a gas flowmeter and a needle valve connected in series. Preferably, a pressure gauge and filter are also included. The valve assembly is powered by the main electrical supply and an input to the valve assembly is connected to an output of the central processing unit (CPU) as shown in FIG. 14 and described further below. The oxygen-containing gas may be any oxygen-containing gas as described above, preferably pure oxygen as fed from an oxygen tank or an in-house oxygen source which is introduced into the system at a pressure of from about 2 to about 10 psig. The oxygen-containing gas and warm gas from the generator 10 are combined to form feed gas. The feed gas is forced by pump 90 into the inlet of the gas side of the heat exchanger 38, as described above, and cooled.

Water, or other suitable coolant, which is preferably filtered, is fed into the sterilizer apparatus 11 through a main water supply line 19 at a pressure of from about 25 to about 50 psig, preferably about 35 psig and at about 65° F. The line 19 is split into two feed lines 21, 23. Line 21 is fed at a regulated water pressure and flow rate through a valve assembly 25 into the second coolant side of the heat exchanger 38. The valve assembly 25 preferably includes a solenoid valve, a water pressure regulator, a needle valve and a switch. As shown in FIG. 14, an output of the CPU is connected to the input of the valve assembly such that water entering the heat exchanger 38 has a regulated pressure of about 25 psig and a flow rate of about 1.7 gallons per minute. The water is fed into the inlet of the second coolant side of the heat exchanger 38, and cooled by a second coolant, such as a refrigerant or refrigerated water, in the first coolant side of the heat exchanger 38 to a temperature of from about 30° F. to about 45° F., preferably from about 30° to about 35° F.

The cold water leaves the outlet of the second coolant side of the heat exchanger 38 and enters line 27 which is connected to the inlet 32 of the cooling jacket of the ozone generator 10 such that the water functions as the first coolant for the generator as described above.

The outlet 36 of the cooling jacket is connected to the first end of line 27a. The second end of line 27a is in fluid communication with the inlet of the second coolant side of the heat exchanger 38. A controlled amount of water substantially equal to the amount of water fed into the heat exchanger through line 21 preferably exits the heat exchanger through a main drain line 29.

Figure 5:
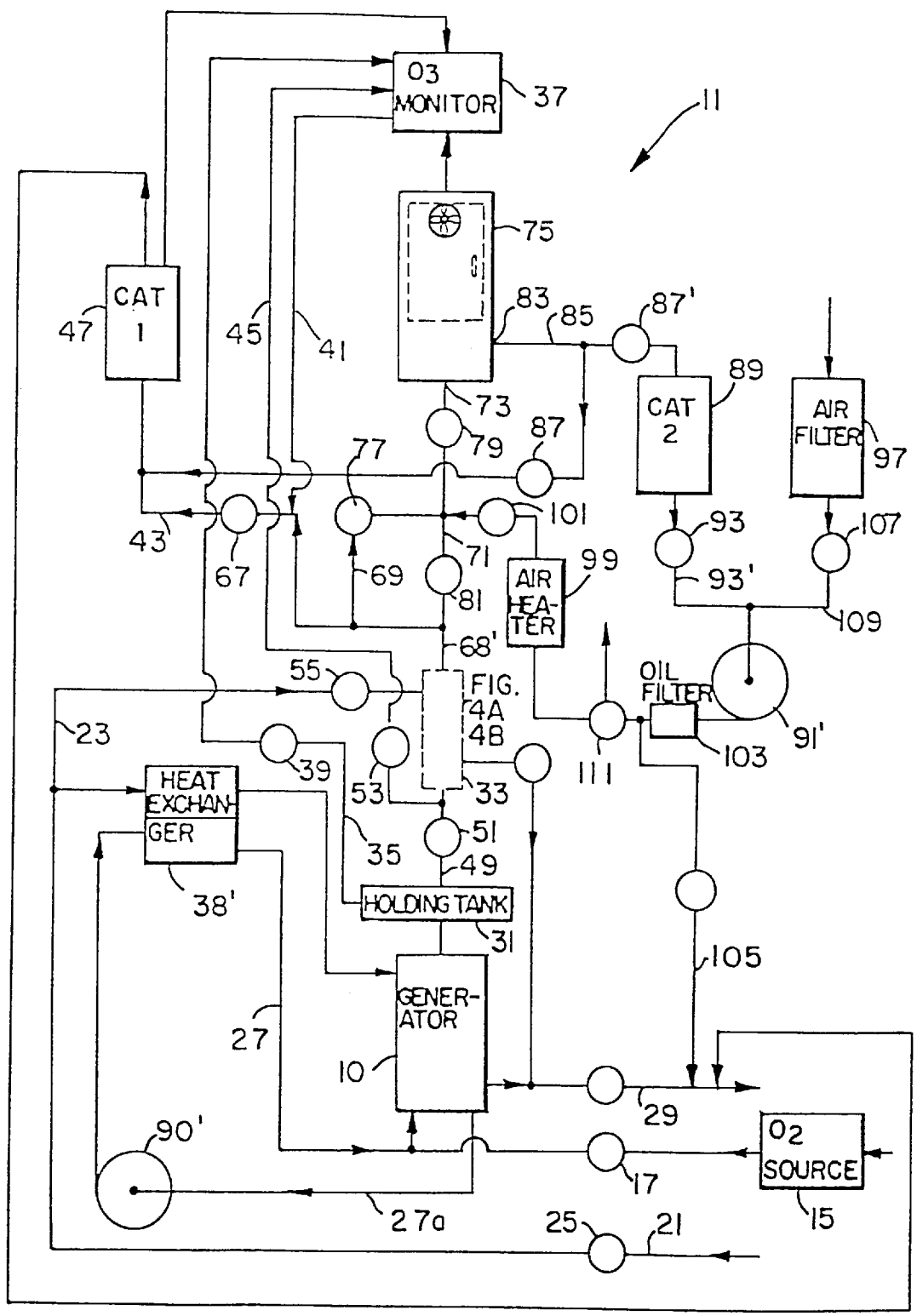
FIG. 5 is a flow diagram of an alternative embodiment of an ozone sterilizer according to the invention.

The outlet of the ozone generator 10 for releasing a gas containing ozone formed in the generator 10 is in fluid communication with a holding tank 31 for receiving the gas containing ozone. The gas is a mixture of feed gas and ozone leaving the ozone generator 10. The gas mixture passes into the holding tank 31 and accumulates prior to introducing the gas into the humidification chamber 33. A first outlet of the holding tank 31 is connected to line 35 which is in fluid communication with an inlet to the ozone monitor 37. The ozone monitor may be any acceptable ozone monitor such as the monitor as described in U.S. Pat. No. 5,167,927 of the present inventor, herein incorporated by reference. The ozone monitor also preferably has input connections, as shown in FIGS. 4 and 5, which measure the ozone concentration in the holding tank 31, the inlet to the humidification chamber, the first catalyst and within the sterilization chamber.

Preferably valve assembly 39 is placed in line 35 and includes a pressure regulator and solenoid valve for regulating a pressure of the ozone-containing gas in line 35. The ozone concentration in the holding tank 31 is detected and measured by the ozone monitor. An outlet of the ozone monitor 37 is connected to line 41 which connects to line 43. Line 43 leads to a first system catalyst 47 such that excess ozone passing outward from the monitor is fed through the catalyst 47 and then to drain line 29. The catalyst 47 destroys the ozone in the sterilant by converting the ozone back to oxygen. The catalyst preferably also includes a heating element. Any catalyst capable of destroying ozone in the sterilant prior to releasing the sterilant gas into a drain may be used. Preferably, the catalyst 47 is a catalyst and heater within a tube including temperature sensors such as that described in U.S. Pat. Nos. 4,988,484, 5,069,880, both of the present inventor and herein incorporated by reference, and 5,167,927. Line 45 is connected between the ozone monitor 37 and line 49 for measuring the concentration of ozone in the gas entering the humidification chamber 33.

The holding tank 31 is preferably in fluid communication with an inlet 49' to the humidification chamber 33 for receiving the ozone-containing gas from the holding tank 31. Line 49 connects the primary outlet line of the holding tank 31 to the inlet 49' of the humidification chamber 33. A check valve 51 is in place between the holding tank 31 and the humidification chamber 33. The function of the check valve 51 is to prevent humidified sterilant from passing backwards into the generator. In the event of a failure of the check valve 51, the humidified sterilant passes backward into the holding tank 31 which preferably accumulates the sterilant before it can enter the generator 10. In the event of such an occurrence, the holding tank 31 is preferably equipped with an emergency drain line (not shown) connected to pass through the first system catalyst 47 and into the drain line 29. A valve may be included in the emergency drain line and the CPU programmed to open the valve when the generator 10 is shut off if a slight vacuum is created in the generator and holding tank 31 due to cooling of the generator. In this manner, water which collects in the holding tank 31 will not be drawn back into the generator 10 and potential leaks can be prevented.

Line 45 preferably includes solenoid valve 53 which functions with the CPU, the ozone monitor 37 and valve assembly 39 for controlling the ozone concentration, flow rate and pressure of the ozone gas mixture leaving the holding tank 31 from the generator and entering the humidification chamber 33.

Figure 4A:
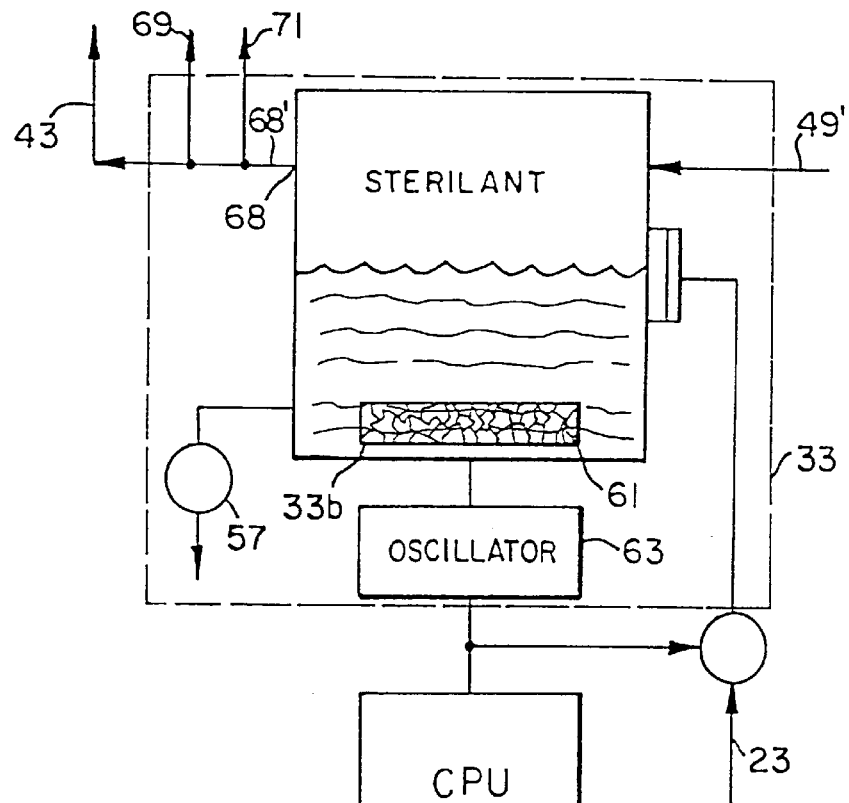
FIG. 4a is a schematic representation of one embodiment of a humidification chamber, within the broken line of FIG. 4.
Figure 4B:
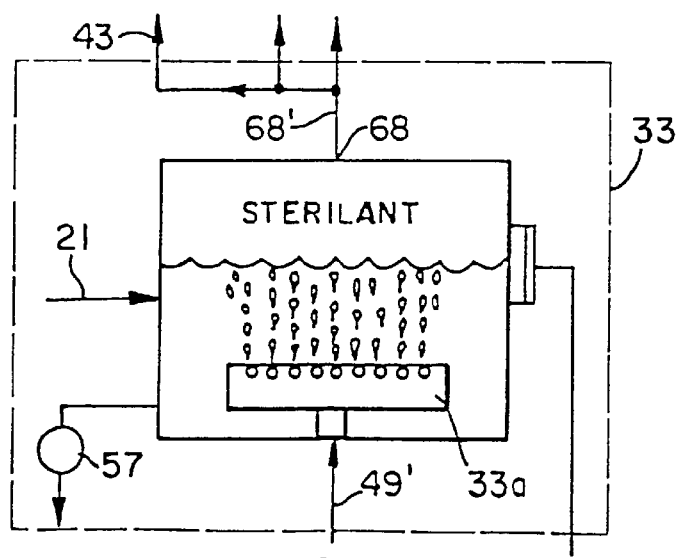
FIG. 4b is a schematic representation of an alternative embodiment of a humidification chamber, within the broken line of FIG. 4.

The water feed line 23 is connected to the humidification chamber 33. Valve assembly 55 which preferably includes a needle valve and solenoid valve is situated in line 23 to control the flow of water which enters the humidification chamber 33. Alternative embodiments of the humidification chamber 33 are shown in FIGS. 4A and 4B. In either embodiment, the humidification chamber 33 preferably includes an adjoining side-chamber, such as a sight glass (not shown) for viewing and measuring the level of water in the chamber 33 and a level controller for controlling the water level received within the chamber 33. The level controller may be any suitable level controller.

As shown in FIG. 4B, the humidification chamber 33 includes a humidifier 33a in the form of a pipe having a plurality of small holes for bubbling the ozone gas mixture through water to humidify the ozonated gas forming the sterilant above the water. Such a humidifier 33a is described in U.S. Pat. No. 5,069,880. The chamber 33 is preferably equipped with a drain line including a solenoid valve 57 in electrical communication with the CPU. This bubbling-type humidifier 33a is simple to make and inexpensive. It functions well in smaller sterilizers. However, if larger sterilizers of at least about 4 ft$^3$ are made according to this invention, or if higher amounts of humidified ozone are required, the bubbling-type chamber is not preferred as there may be too great a loss of ozone in the water bath.

An alternative embodiment of the humidification chamber is shown in FIG. 4A. The ozone gas mixture is not bubbled through the water bath in this embodiment such that there is a very small loss of ozone in the humidification chamber 33. In FIG. 4A, the chamber 33 includes a level controller as shown in FIG. 4B. However, in place of a pipe for bubbling the ozone gas mixture through water, the chamber 33 includes a humidifier 33b having an ultrasonic vibrating cell 61. The cell may be any suitable ultrasonic cell such as, for example, a piezoelectric ceramic crystal, including potassium, barium titanite, lead zirconate, diamond, quartz and the like. The crystal 61 is connected to the output of an oscillator 63 for vibrating the cell. The input of the oscillator 63 is connected to an output of the CPU, preferably to the same portion of the CPU which functions to control the water level in the humidification chamber 33.

In this embodiment, the ozone gas mixture is not fed through the water bath, but passed over the top of the water bath. The oscillator frequency vibrates the crystal which is below a controlled water level. The vibration of the water creates a vapor above the water. Preferably, a 50 KC oscillator vibrating at a frequency of from about 30,000 to about 100,000 Hz, preferably from about 70 kHz to about 80 kHz is used in this embodiment. The vapor combines with and humidifies the ozonated gas passed over the water bath forming the sterilant. The humidification level can be controlled by varying the vibration frequency of the oscillator 63 as controlled by the CPU. The higher the frequency, the higher the relative humidity of the sterilant. As such, this embodiment offers the advantages of maximizing the ozone concentration in the sterilant and providing a high level of humidification control.

The sterilant leaves the humidification chamber 33 having a temperature of from about 45° F. to about 90° F. and a concentration of ozone of from about 8% to about 15% by weight, preferably about 10% to about 15% by weight and more preferably about 12% to about 15% by weight at a relative humidity of from about 60% to about 99%, and preferably from about 80% to about 95%. The temperature of the ozone sterilant is preferably from about 45° F. to about 80° F. when it enters the sterilization chamber 75, although it may be slightly more or less depending upon the temperature of the sterilant leaving the humidification chamber and the rate at which the sterilant is introduced to the sterilization chamber through the bypass valve. Sterilant at temperatures of up to about 100° F. provides an effective bacteria kill rate and faster kill time than colder sterilant. At a sterilant concentration of from about 8% to about 15% ozone by weight as delivered by the invention, bacterial kill times of only 25 minutes for *Bacillus Subtelis* (globigii) at a D star of 4.5 minutes have been achieved.

Preferably, a flow of sterilant from the humdification chamber 33 passes through a first vent by flowing the sterilant through line 43. The flow is controlled by valve assembly 67 which preferably includes a needle valve, a solenoid valve and a flowmeter. Line 43 is also connected to the catalyst 47 for continuous bleeding of the humidification chamber 33 through line 43 when the valve assembly 67 is open.

The sterilant is released from the humidification chamber 33 through outlet 68 as shown in FIGS. 4A and 4B. Line 68' splits to lines 43, 69 and 71. Line 43 is the vent line for the chamber 33. Line 69 is a bypass line and line 71 is a direct line, both of which are for introducing sterilant to the sterilization chamber. The outlet 68 of the humidification chamber 33 is in fluid communication with the inlet 73 of the sterilization chamber 75 which receives the sterilant from the humidification chamber.

The chamber 75 preferably includes an outer wall portion enclosing an interior space 75' for receiving items to be sterilized therein. In the embodiment as shown, the sterilization chamber 75 includes a motorized door which slidably moves with respect to the wall portion of the chamber. The motorized door is in electrical communication with the CPU such that the door opens automatically when a sterilization cycle is over and the ozone monitor detects a safe level of ozone. The door closes upon receiving an input from an operator of the apparatus that they wish to start a sterilization cycle. The door hermetically seals during the cycle, and preferably locks from the inside, and cannot be opened manually unless the ozone level within the chamber is at a safe level. Preferably, the chamber 75 is also equipped with a rupture disk or other safety valve to allow the chamber 75 to vent through one of the system catalysts in the event of an accidental pressure build-up due to valve failure.

The flow of sterilant into the sterilization chamber is controlled by means for controlling the flow of sterilant positioned in communication with the inlet 73 of the chamber. As shown in FIG. 4, the sterilant may enter the sterilization chamber 75 through bypass line 69 which allows for a metered flow of sterilant into the chamber 75. The metered flow is provided such that a large pressure change created by evacuating the sterilization chamber 75 prior to the sterilizing process does not harm the ozone gas sterilant which is introduced into the sterilization chamber. The bypass line 69 includes valve assembly 77 which preferably includes a needle valve and solenoid valve. The metered flow of sterilant then passes through solenoid valve 79 into the chamber 75.

When the chamber 75 is at ambient pressure as detected by pressure sensors within the sterilization chamber and a pressure detector in electrical communication with the CPU, the valve assembly 77 is closed and sterilant leaves the humidification chamber through line 71 and enters the chamber 75 at a full, unrestricted flow rate. Solenoid valve 81 is positioned in line 71 between the humidification chamber 33 and the valve to the sterilization chamber 75. Valve 81 is closed during bypass flow such that the sterilant passes through valve assembly 77. When bypass flow is complete and the pressure is ambient, valve 81 is opened. Once unrestricted flow through valves 81 and 79 is in place, bypass valve 77 is closed and sterilant is continuously bled from the sterilization chamber 75 through a second vent over the first catalyst 47 which is in fluid communication with the outlet 83 of the sterilization chamber 75. The second vent for the sterilant, as shown in FIG. 4, may include passing the sterilant outward through line 85 and solenoid valve 87. As shown in FIG. 4, line 85 is connected to line 43. The sterilant is circulated throughout the chamber by an internal fan, blower or similar means for gas circulation. Preferably, the sterilization chamber is configured such that the circulation means is an internal fan provided within a back wall portion of the chamber. The temperature and pressure in the sterilization chamber 75 are continuously monitored during the operation of the sterilizer by temperature and pressure sensors located within the chamber. The sensors are in electrical communication with pressure and temperature detectors powered by the main electrical supply and which supply an electrical signal to the CPU.

Upon completion of the sterilization cycle, or before a sterilization cycle, the sterilization chamber 75 is evacuated through solenoid valve 87' over a second catalyst 89 by drawing the sterilant from the chamber by pump means such as the pump 91. The pump 91 is also in fluid communication with the outlet 83. A safety valve 93, such as a pressure relief valve, is preferably placed in line 93' between the catalyst 89 and the pump 91. The pump 91 may include an ozone resistant material. Due to the presence of the catalyst, however, a non-ozone resistant vacuum pump may be used, as the catalyst operates to destroy ozone prior to passing the gas through the vacuum pump and out of the system. Typical vacuum pumps are not capable of continually producing an acceptable vacuum if pumping a gas containing high concentrations of ozone, however, the presence of the catalyst 89 allow for any suitable vacuum pump to be used.

After a period of time, water from the evacuated sterilant gas collects in a collector at the bottom of the pump. The water and oil collected in the base of the pump leave the pump 91 and pass through an oil separator 95. The oil separator includes a hollow chamber and drip line. Water collects and separates from the oil and may be emptied into the main drain line 29 through line 93'. The oil phase can be recirculated as pump oil after separation. Alternatively, the oil and water collected at the base of the pump may be heated to remove water from the oil phase.

At the end of the sterilization cycle, after evacuation of the sterilization chamber, the pump 91 operates to draw warm, filtered air through the chamber 75 to dry the sterilized articles and to ensure that all sterilant is removed from the chamber 75 prior to opening the chamber to remove the articles. Outside air which is passed through an air filter 97, such as, for example, a HEPA® biomedical air filter, is drawn through a heater 99 and warmed to a temperature of about 110° F. The warm air flows through solenoid valve 101, line 71 and valve 79 into the chamber 75 where it is circulated by a fan, blower, or the like, as described above.

In an alternative embodiment of the sterilizer apparatus, as shown in FIG. 5, the incoming water line 21 after the valve assembly 25 enters the first coolant side of the heat exchanger at a chilled temperature of 35° F. and acts as both the first and second coolants in the heat exchanger 38'. The chilled water cools the recirculated mixture of feed gas and ozone leaving the generator 10 and forced through the inlet of the gas side of the heat exchanger by pump 90'. The cooled gas leaving the heat exchanger is combined with an oxygen-containing gas from source 15 to form feed gas which is fed to the ozone generator 10. The chilled water which leaves the heat exchanger at a temperature of 40° F. is further used as the first coolant in the cooling jacket of the ozone generator.

As shown in FIG. 5, the vacuum pump 91' is situated such that it functions to force outside air through the sterilizer at the end of the sterilization cycle instead of drawing the air through the sterilizer as in the apparatus of FIG. 4. The pump 91' further functions to evacuate the sterilization chamber 75 over the second system catalyst 89, through line 93' and an oil filter 103, which removes any particles of pump oil or water which may have been introduced into the filtered air by the pump. The oil filter may be any suitable oil filter, or an oil separator as described above. After filtration, the evacuated sterilant, or other gas, may pass directly into the drain line 29 through line 105.

After sterilization, during the aeration cycle, air is drawn into the system by pump 91' through air filter 97, and passes through solenoid valve 107 in line 109. The air then passes through oil filter 103 and solenoid valve 111 into the air heater 99. After warming the filtered air, the air passes into the inlet 73 of chamber 75 through valves 101 and 79. The air leaves the chamber 75 through outlet 83, line 85 and valve 87 and is passed over the first system catalyst 47.

Aside from the heat exchanger and pump system, in all other respects, the apparatus of FIG. 5 is the same as that shown in FIGS. 4, 4A and 4B.

In the embodiments of FIGS. 4, 4A, 4B and 5, the electrical control system includes a main electrical supply or distribution bus which is preferably a 120V AC source as shown in FIG. 14. The electrical power is used to operate the primary electrical components of the apparatus, including the cooling system, which includes the heat exchanger and pump or other forcing means; the heater, the chamber fan or other circulation means for the sterilization chamber; the vacuum pump; the door motor for operating the automatic door of the sterilization chamber; the CPU; the electrically operable valves, regulators, sensors and detectors; and the frequency drive controller, transformer and ozone generator.

The CPU may be any standard central processing unit which preferably has random access and non-volatile memory capacity, such as, for example, an OMRON® Model 41-E. The CPU may also include a keyboard for entering sterilization data for processing various sized loads, such as the desired sterilization cycle time and number of cycles, the required ozone concentration or oscillator frequency set points. The keyboard may also be used for entering programming information for pre-programming the apparatus. The CPU may optionally include a display terminal, modem or printer as shown in FIG. 14. The sterilizer may further include an ABORT button on the keyboard such that in the event the operator needs to terminate a sterilization cycle, the CPU can turn off the power and vent the system over the catalyst 89 as described below with respect to the sterilization method.

The output of the CPU is connected to the various control valves regulators, sensors and detectors such that the CPU may operate the control valves and regulators in response to signals from the temperature and pressure sensors and detectors, as described below. The CPU also operates various control valves during different phases of the sterilization cycle, as described below, in response to the ozone concentration as measured at various locations in the system by the ozone monitor which has an output connected to an input of the CPU.

The output of the CPU is also connected to the controlling means for the ozone generator. As shown in FIG. 14, the CPU output may be connected to the input of an oscillator which operates to proportionally control the frequency drive controller which operates the transformer. The transformer powers the generator as described above with respect to the ozone generator 10. In this embodiment, the ozone concentration in the holding tank is controlled by programming the CPU to vary the oscillation frequency of the oscillator between a set minimum and maximum value, entered into the CPU, in proportion to the desired ozone concentration maximum and minimum values as monitored by the ozone monitor.

Alternatively, as shown by the dotted line in FIG. 14, the ozone concentration is controlled by the on-off operation of the frequency drive controller (operating at a constant frequency) as electrically operated by AC voltage from the CPU through a DC rectifier as described above. The ozone concentration is controlled by stopping the input of voltage to the frequency drive controller when the ozone concentration in the holding tank is greater than 15% by weight and increasing the voltage input to the frequency drive controller when the concentration in the holding tank is less than 8% by weight, however, the concentration control range may be narrowed, for example between 10% and 15% by weight. The concentration set points may be programmed into the CPU such that it functions automatically once the sterilization cycle time and number of cycles are entered.

Figure 16:
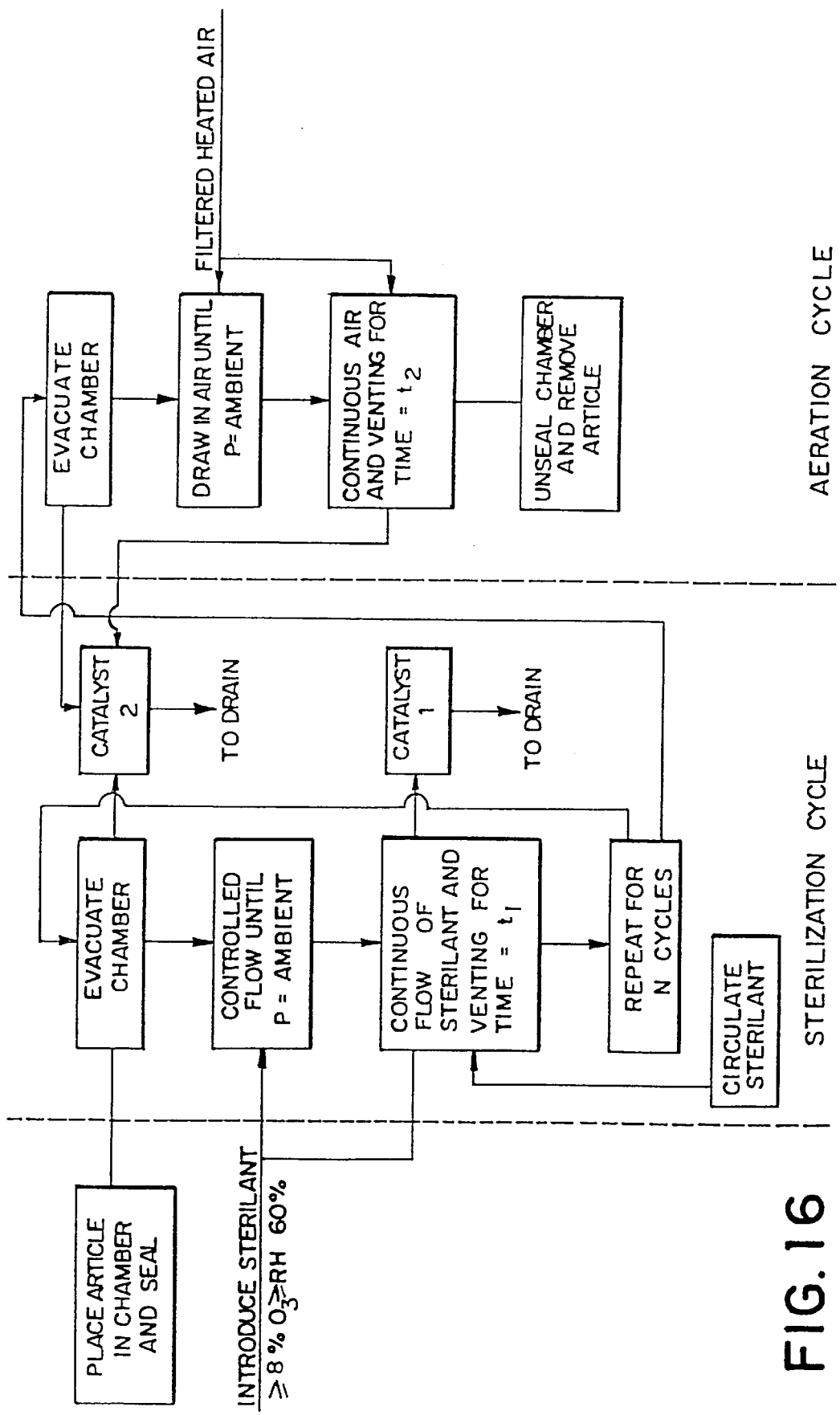
FIG. 16 is a flow diagram of a method for sterilizing articles in accordance with an embodiment of the invention.

The invention also includes a method for sterilizing an article. One embodiment of the method is represented in the flow diagram of FIG. 16 and will be described with reference to that Figure and the embodiment of the sterilizer 11 as shown in FIG. 4. Articles are placed in a sterilization chamber of an apparatus such as the sterilizer 11 described above. The articles may be placed in a basket or set on optional shelves provided to the sterilization chamber. The articles are preferably wrapped or enclosed in gas permeable packages. The articles may be placed in the chamber without wrapping. The chamber is automatically sealed upon closing the chamber door. After sealing the chamber, the chamber is evacuated to a pressure of about 50 microns beginning a first sterilization cycle. The vacuum level is generally high in order to free air which may be trapped in apertures, crevasses, holes and the like.

The time for sterilizing a particular load of articles can be entered into the CPU upon closing the chamber door. As soon as the sterilization time is entered and the door sealed, the sterilization process begins.

Preferably, during the evacuation of the sterilization chamber, ozone is being generated in at least one ozone generator, preferably the ozone generator 10 or multiple generator apparatus 104 as described above. The ozone generated during the evacuation of the chamber flows through the open lines and chambers of the system up to and including the humidification chamber 33 in which the sterilant is formed. At this point, valves 81, 77 and 79 which control introduction of the sterilant into the chamber 75, and the sterilization bleeding valve 87 are closed. During this period, ozone sterilant is continuously vented from the humidification chamber in vent line 43 through valve 67 and out of the system over the first system catalyst 47. When the full vacuum level is reached, the pressure detector signals the CPU that the evacuation is complete and the CPU will shut the power input to the vacuum pump 91, thereby stopping the pump. The CPU will also close valves 87' and sterilant bleeding valve 67 as shown in FIG. 4 and open valves 79 and 77 in bypass line 69 to begin slowly introducing sterilant into the chamber 75.

When the pressure detector signals the CPU that the pressure in the chamber 75 has reached ambient, the CPU will operate to open valve 81 and close valve 77 such that full flow of sterilant into the chamber 75 is provided. At the same time that valve 81 is opened, the CPU will signal to open valve 87 such that continuous full flow of sterilant through the chamber 75 is accomplished while also continuously bleeding sterilant from the chamber at a controlled rate through line 85 and out of the system over catalyst 47.

A controlled flow of sterilant gas having an ozone concentration of at least 8% by weight and relative humidity of at least 60%, as described above, flows through the chamber for a predetermined period of time=$t_1$. The sterilant is circulated within the chamber during the whole of the first sterilization cycle. At the end of the sterilization cycle, the chamber is again evacuated and the sterilization cycle repeated for a number of cycles=N. The sterilization time $t_1$ and the number of cycles N are determined based upon the size and quantity of the articles to be sterilized and the degree of contamination. Heavier sterilization loads will require longer cycles. Sterilization times typically vary from about 10 min. to about 40 min., preferably from about 5 min. to about 15 min. depending upon the quantity of articles to be sterilized and whether the articles are wrapped or unwrapped. The number N of cycles generally varies from about 2 to about 6, preferably about 3.

Once the first cycle is complete, i.e., time $t_1$ has expired, the CPU will operate to close valves 87, 81 and 79, open valves 67, 87' and 93 and to start pump 91. The pump will again evacuate the chamber 75 over catalyst 89 while the sterilant is continuously vented through line 43 over catalyst 47. When the vacuum level is reached, the sterilization cycle is repeated for N cycles as described above. Each of the N cycles can be automatically programmed to have the same sterilization time $t_1$. The number of cycles will vary with the quantity of articles to be sterilized.

Once the sterilization cycle is complete, the aeration cycle begins. The power to the ozone generator 10 is terminated by the CPU and no further ozone is generated. The cooling system is also stopped and water in the humidification chamber 33 is drained through valve 57. Valves 87, 81 and 79 are closed and valves 87' and 93 are opened by the CPU. The chamber 75 is again evacuated by pump 91 through oil separator 95 to a level of about 50 microns over the second system catalyst 89. When the vacuum level is reached, valves 101 and 79 are opened and filtered, heated air, which is bacteria-free, is continuously drawn into the sterilization chamber by pump 91 and vented over the second system catalyst 89 for a second predetermined period of time $t_2$ sufficient to extract all traces of ozone from the chamber and articles.

After the time $t_2$, if ozone is still detected in the chamber 75 by the ozone monitor 37, then the chamber door will not open and the aeration cycle will automatically repeat until there is no ozone detected in the chamber. The average aeration time $t_2$ is from about 3 min to about 10 min, preferably from about 5 min to about 10 min.

After the chamber is fully aerated, as confirmed by the ozone monitor, an indicator light will alert the operator that the ozone level is safe and the CPU will automatically actuate the motor which opens the door to the chamber and unseal the chamber. The articles can then be removed from the chamber.

The invention will now be described in more detail with respect to the following specific, non-limiting examples:

EXAMPLE I

A model heat exchanger was constructed based upon the embodiment of the heat exchanger as shown in FIG. 5 in which the heat exchanger has a gas side and a first coolant side. The model heat exchanger included a total flow length of 28 in. It included a gas side formed of a stainless steel, inner, cylindrical tube having an inner diameter of 0.75 in. and a wall thickness of 0.025 in. The heat exchanger also included a first coolant side in the form of a stainless steel, outer, cylindrical tube which was positioned around the inner tube. The outer tube had an inner diameter of 1.75 in. and a wall thickness of 0.050 in. The end plates for the heat exchanger also were formed of stainless steel. No external insulation was provided.

The metal chips which were provided to the interior of the gas side of the heat exchanger were copper chips which were roughly semi-circular in configuration and ¾ inch long as measured in the longest dimension. Each chip had an external flat surface. The thickness of the chips ranged from 1/16 in. to ⅛ in.

A series of heating experiments were performed using the heat exchanger to heat air at 3 p.s.i. Hot water was passed through the outer tube at three different flow rates. The temperature of the water in the outer tube and the air in the inner tube was continuously monitored by five individual Omega 0.1% precision platinum thermocouples. The flow of gas and water was monitored by two precision 1.0% Honeywell flowmeters. Three readings were taken from each flowmeter and then averaged. Several runs were performed and readings were taken with and without the use of metal chips. The data for the experiments without the chips are shown below in Table I, and the data for the experiments with the chips are shown below in Table II:

TABLE I

| Air Flow Rate (l/min) | Water Flow Rate (gal/h) | Water Temp. (°F.) | | Air Temp. (°F.) | | Temp. Rise (°F.) | Air Pressure Drop (psi) |
|---|---|---|---|---|---|---|---|
| | | In | Out | In | Out | | |
| 6 | 15 | 107 | 106 | 71.2 | 85.5 | 14 | 0 |
| 6 | 20 | 108 | 106.4 | 72.9 | 91.5 | 18 | 0 |
| 6 | 30 | 109 | 107.2 | 73.9 | 96.7 | 23 | 0 |

TABLE II

| Air Flow Rate (l/min) | Water Flow Rate (gal/h) | Water Temp. (°F.) | | Air Temp. (°F.) | | Temp. Rise (°F.) | Air Pressure Drop (psi) |
|---|---|---|---|---|---|---|---|
| | | In | Out | In | Out | | |
| 13 | 15 | 112 | 108.0 | 66.3 | 100 | 33.7 | 0.5 |
| 13 | 20 | 112.8 | 107.2 | 66.4 | 105 | 37.8 | 0.5 |
| 13 | 30 | 115 | 110.5 | 66.3 | 108.9 | 42.6 | 0.5 |

EXAMPLE II

Using the model heat exchanger of Example I, a series of cooling experiments were performed using the heat exchanger as an air chiller for 3 p.s.i. air. Dry ice was packed within the outer tube and air was circulated through the inner tube at varied flow rates. The experiments were performed with and without the metal chips of Example I, and readings were taken every 5 minutes. The data for the experiments without metal chips are shown below in Table III and the data for the experiments with metal chips are shown below in Table IV:

TABLE III

| Air Flow Rate (l/min) | Dry Ice Temp. (°F.) | | Air Temp. (°F.) | | Temp. Drop (°F.) | Air Pressure Drop (psi) | Time (min) |
|---|---|---|---|---|---|---|---|
| | In | Out | In | Out | | | |
| 9 | −97 | −97 | 68.5 | 5.9 | 62.6 | 0.5 | 5 |
| 9 | −97 | −97 | 67.4 | 6.0 | 61.4 | 0.5 | 10 |
| 9 | −97 | −97 | 67.6 | 4.4 | 63.2 | 0.5 | 15 |
| 9 | −97 | −97 | 66.9 | 3.4 | 63.5 | 0.5 | 20 |

TABLE IV

| Air Flow Rate (l/min) | Dry Ice Temp. (°F.) | | Air Temp. (°F.) | | Temp. Drop (°F.) | Air Pressure Drop (psi) | Time (min) |
|---|---|---|---|---|---|---|---|
| | In | Out | In | Out | | | |
| 9 | −97 | −97 | 67.4 | −17 | 84.4 | 0.5 | 5 |
| 9 | −97 | −97 | 66.6 | −20.1 | 86.7 | 0.5 | 10 |
| 9 | −98 | −98 | 67.6 | −28.8 | 96.4 | 0.5 | 15 |
| 9 | −99 | −99 | 67.0 | −31.4 | 98.4 | 0.5 | 20 |
| 9 | −99 | −99 | 67.5 | −36.5 | 104.1 | 0.5 | 25 |
| 9 | −99 | −99 | 66.8 | −37.0 | 103.8 | 0.5 | 30 |
| 9 | −99 | −99 | 67.1 | −36.8 | 103.9 | 0.5 | 35 |

As can be seen from Examples I and II, the addition of the metallic bodies significantly increase the thermal transfer as measured by temperature change over the heat exchanger. In most cases, the efficiency of the thermal transfer in various heat exchanger applications will depend on the type of metallic bodies used, the fluid barrier, the temperature ranges of the heat exchange fluids, the type of fluids and their flow rates through the heat exchanger.

EXAMPLE III

A sterilizer in accordance with the embodiment shown in FIG. 4 was used for testing the required kill time for a various common bacteria. The sterilizer unit was 5 ft³ in overall size including the ozone generators. The sterilizer included a multiple generator unit having two generators forming ozone from feed gas formed from pure oxygen and a recirculated portion of a mixture of the feed gas and ozone exiting the zones of the generators. The generators delivered to the sterilization chamber an ozone sterilant with an average ozone concentration of 10% by weight ozone at 95% relative humidity. The ozone concentration was controlled by use of a variable frequency drive controller operating at frequencies between 300 and 400 Hz which controlled a transformer having an input of 160 V at 10–15 amps. The humidifier was made in accordance with the embodiment shown in FIG. 4B with the crystal vibrating at a frequency of 70,000 Hz.

In accordance with governmental sterilization standards, kill time was determined by providing a 10 min dose of sterilant to the sterilizer having $10^6$ bacteria on stainless steel carrier strips once the sterilizer is at ambient conditions. 50 samples were run with varied times and kill rate increased until the kill rate approached zero. A graph of number of bacteria v. kill time is prepared and the time corresponding to zero bacteria is used as the experimental kill time. As even a zero bacterial count from such an approximation may result in a few remaining bacteria due to calculational and operational error, the experimental kill time is then doubled to determine the actual kill time for use in the sterilizer. The kill times for the sterilizer are shown below in Table V for various common bacteria. Based on the foregoing, the kill times represent the twice the time necessary to kill $10^6$ bacteria with a maximum dosage of 10% by weight humidified ozone at a relative humidity of 95% on stainless steel carrier strips.

TABLE V

| Bacteria Type | Test Organism | Kill Time (min) |
|---|---|---|
| Bacterial Spores | *Bacillus subtilis* ATCC 9372 | 35 |
| Bacterial Spores | *Bacillus stearothermophilus* | 35 |

TABLE V-continued

| Bacteria Type | Test Organism | Kill Time (min) |
|---|---|---|
| | ATCC 12980 | |
| Bacterial Spores | Clostridium sporogenes ATCC 3584 | 40 |
| Mycobacteria | Mycobacteria tuberculosis var. bovis | 12 |
| Fungi | Trichophyton Mentagrophytes ATCC 9533 | 10 |
| Vegetative Bacteria | Pseudomonas aeruginosa ATCC 15442 | 10 |
| Vegetative Bacteria | Staphylococcus aureus ATCC 6538 | 11 |
| Vegetative Bacteria | Salmonella cholerasius ATCC 10708 | 10 |
| Lipid Virus | Herpes Simplex Virus Type 1 ATCC VR-733 | 15 |
| Nonlipid Virus | Poliovirus Type 1 ATCC VR-192 | 15 |

As the results show, the kill time (even when doubled for safety and regulatory reasons) is extremely short in comparison with prior art ethylene oxide sterilizers. In addition, the sterilizer provided a quick aeration time on the average of about 10 min. A full sterilization cycle was complete in an average time of under 2 hours. The kill rate for all samples was 100%.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the invention as defined by the appended claims.

I claim:

1. An ozone sterilizer, comprising:
   (a) an ozone generator capable of generating a gas comprising at least about 10% by weight ozone, comprising:
      (i) an ozone generation zone having a feed gas inlet;
      (ii) a first outlet for releasing a first portion of gas leaving the ozone generation zone; and a second outlet for releasing a second portion of gas leaving the ozone generation zone;
      (iii) a heat exchanger having an inlet in communication with the first outlet of the generation zone and an outlet in communication with the feed gas inlet; and
      (iv) an inlet for introducing a gas comprising oxygen into the first portion of the gas to form a feed gas for introducing into the feed gas inlet;
   (b) a holding tank in fluid communication with the ozone generator for receiving the gas comprising ozone therefrom and for preventing backflow of moisture to the generator;
   (c) a humidification chamber in fluid communication with the holding tank for receiving the gas comprising ozone therefrom, the humidification chamber having a humidifier for humidifying the gas comprising ozone to form a sterilant comprising at least about 8% by weight ozone at a humidity of at least about 60%;
   (d) a first catalyst and a first vent for bleeding the sterilant from the humidification chamber over the first catalyst for converting ozone to oxygen, wherein the first catalyst is in fluid communication with the first vent;
   (e) a sterilization chamber in fluid communication with the humidification chamber for receiving the sterilant therefrom;
   (f) a second vent for bleeding the sterilant from the sterilization chamber over the first catalyst, wherein the second vent is in fluid communication with the sterilization chamber and the first catalyst;
   (g) means for controlling gas flow from the humidification chamber to the sterilization chamber;
   (h) a heater in communication with the sterilization chamber for providing warm air to the sterilization chamber;
   (i) a second catalyst; and
   (j) pump means in fluid communication with the heater and the second catalyst for flowing air into the sterilization chamber and for evacuating the sterilization chamber over a second catalyst for converting ozone to oxygen.

2. The apparatus according to claim 1, wherein the ozone generator is capable of generating a gas comprising at least about 14% by weight ozone and the sterilant comprises at least about 10% by weight ozone at a humidity of at least about 60%.

3. The apparatus according to claim 1, comprising a plurality of ozone generators having outlets in fluid communication with the holding tank.

4. The apparatus according to claim 1, wherein the ozone generator further comprises a first electrode and a second electrode spaced from each other and defining between them an ozone generation zone.

5. The apparatus according to claim 4, wherein the generator further comprises means for circulating the feed gas through the heat exchanger and the zone.

6. The apparatus according to claim 5, wherein one surface of the first electrode is in heat exchange relation with a first coolant and one surface of the second electrode is in heat exchange relation with the second portion of the feed gas directed away from the zone.

7. The apparatus according to claim 1, further comprising a check valve between the holding tank and the humidification chamber.

8. The apparatus according to claim 1, further comprising means for controlling a concentration of ozone in the holding tank from at least about 8% by weight to no greater than about 15% by weight.

9. The apparatus according to claim 8, wherein the ozone concentration control means comprises a central processing unit electrically connected to a voltage source at a constant frequency, the voltage source electrically connected to a power source for the generator, the central processing unit being programmed to stop input of voltage to the power source when the ozone concentration in the holding tank is greater than 15% by weight and to start the input of the voltage to the power source when the concentration in the holding tank is less than 8% by weight.

10. The apparatus according to claim 8, wherein the ozone concentration control means comprises a central processing unit electrically connected to an oscillator for varying a frequency of a voltage source, the voltage source electrically connected to a power source for the generator, the central processing unit being programmed to proportionally vary the frequency between a minimum level and a maximum level in response to changes in a measured concentration of ozone in the holding tank.

11. The apparatus of claim 1, further comprising an ozone monitor electrically connected to a central processing unit and connected to the holding tank, an inlet to the humidification chamber, the first catalyst and an inlet to the sterilization chamber.

12. The apparatus according to claim 1, wherein the humidifier further comprises a conduit having a plurality of apertures therethrough configured for bubbling the gas comprising ozone through water received within the humidification chamber and a level controller for controlling a level of water received within the humidification chamber.

13. The apparatus according to claim 1, wherein the humidifier comprises an ultrasonic cell connected to an oscillator for vibrating the cell for releasing vapor, the vapor for combining with the gas comprising ozone received within the humidification chamber, and a level controller for controlling a level of water received within the humidification chamber.

14. The apparatus according to claim 13, wherein the cell comprises a piezoelectric ceramic crystal selected from the group consisting of barium titanate and lead zirconate.

15. The apparatus of claim 1, wherein the sterilization chamber comprises an interior space for receiving an article to be sterilized therein, a motorized door slidably attached to the chamber and a fan.

16. The apparatus according to claim 1, wherein the pump means comprises a pump positioned between the second catalyst and an oil separator for drawing air through a biomedical air filter, the heater, and the second catalyst and for forcing the air out of the sterilizer through the oil separator, the oil separator being in fluid communication with a drain line.

17. The apparatus according to claim 1, wherein the pump means comprises a pump for drawing air through a biomedical air filter and for forcing the air through an oil filter and the heater into the sterilization chamber, the pump being in fluid communication between the biomedical air filter and the oil filter and the oil filter being in fluid communication between the pump and the heater.

18. A method for sterilizing an article, comprising the steps of:
   (a) placing an article in a sterilization chamber and sealing the chamber;
   (b) at least partially evacuating the chamber to begin a sterilization cycle;
   (c) generating a gas comprising ozone by:
      (i) introducing a feed gas comprising oxygen into an ozone generation zone between a first electrode and a second electrode in an ozone generator;
      (ii) creating a corona discharge between the first electrode and the second electrode to generate ozone from the feed gas within the zone;
      (iii) cooling a surface of the first electrode with a first coolant;
      (iv) releasing a mixture of the ozone and the feed gas from the zone;
      (v) drawing a portion of the mixture released from the zone through a heat exchanger to cool the mixture; and
      (vi) combining the portion of the mixture with a gas comprising oxygen to form the feed gas;
   (d) humidifying the gas comprising ozone to form a sterilant gas comprising at least about 8% by weight ozone at a humidity of at least 60%;
   (e) introducing into the chamber a controlled flow of the sterilant gas until the chamber is at about ambient pressure;
   (f) circulating the sterilant in the chamber;
   (g) continuously flowing the sterilant into the chamber after ambient pressure is reached for a first predetermined time period and simultaneously bleeding the sterilant from the chamber over a first catalyst for converting ozone to oxygen;
   (h) repeating steps (b) through (g) for a predetermined number of sterilization cycles;
   (i) evacuating the chamber over a second catalyst to begin an aeration cycle;
   (j) drawing filtered, heated air into the chamber until the chamber is at about ambient pressure;
   (k) continuously flowing the heated air into the chamber after ambient pressure is reached for a second predetermined period of time and simultaneously bleeding the air from the chamber over the second catalyst for converting ozone to oxygen;
   (l) unsealing the chamber; and
   (m) removing the article from the sterilization chamber.

19. The method according to claim 18, wherein step (c) further comprises generating ozone in a plurality of ozone generators and step (d) further comprises humidifying the ozone generated in the plurality of generators forming the sterilant prior to introducing the sterilant to the sterilization chamber.

* * * * *